US008712504B2

(12) United States Patent
Godavarty et al.

(10) Patent No.: US 8,712,504 B2
(45) Date of Patent: Apr. 29, 2014

(54) HAND-HELD OPTICAL PROBE BASED IMAGING SYSTEM WITH 3D TRACKING FACILITIES

(75) Inventors: Anuradha Godavarty, Miami, FL (US); Steven A. Regalado, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 983 days.

(21) Appl. No.: 12/625,476

(22) Filed: Nov. 24, 2009

(65) Prior Publication Data
US 2010/0155599 A1 Jun. 24, 2010

Related U.S. Application Data

(63) Continuation-in-part of application No. 12/442,505, filed as application No. PCT/US2007/079906 on Sep. 28, 2007.

(60) Provisional application No. 61/118,326, filed on Nov. 26, 2008, provisional application No. 60/847,812, filed on Sep. 28, 2006.

(51) Int. Cl.
*A61B 6/00* (2006.01)

(52) U.S. Cl.
USPC ............ 600/473; 600/407; 600/425; 600/430

(58) Field of Classification Search
USPC .......................... 600/407, 424, 425, 426, 429
See application file for complete search history.

(56) References Cited

U.S. PATENT DOCUMENTS

| 5,730,133 | A | 3/1998 | Godik |
| 5,830,145 | A | 11/1998 | Tenhoff |
| 5,971,997 | A * | 10/1999 | Guthrie et al. ................ 606/130 |
| 6,795,195 | B1 | 9/2004 | Barbour et al. |
| RE38,800 | E | 9/2005 | Barbour |
| 8,070,682 | B2 | 12/2011 | Zhu |
| 2002/0045811 | A1 | 4/2002 | Kittrell et al. |
| 2002/0050988 | A1 * | 5/2002 | Petrov et al. .................. 345/418 |
| 2004/0215072 | A1 | 10/2004 | Zhu |
| 2004/0254464 | A1 | 12/2004 | Stribling |
| 2005/0116179 | A1 | 6/2005 | Aguirre et al. |
| 2007/0219450 | A1 | 9/2007 | Azar et al. |

FOREIGN PATENT DOCUMENTS

DE 10 2005 058598 A1 7/2006

OTHER PUBLICATIONS

"Ultrasound-Guided Optical Tomographic Imaging of Malignant and Benign Breast Lesions: Initial Clinical Results of 19 Cases" by Q. Zhu et al. Neoplasia. vol. 5, No. 5. 2003. pp. 379-388.*
Culver, J.P. et al., "Three-Dimensional Diffuse Optical Tomography in the Parallel Plane Transmission Gemoetry: Evaluation of a Hybrid Frequency Domain/Continuous Wave Clinical System for Breast Imaging," *Medical Physics*, 30(2):235-47 (Feb. 2003).

(Continued)

*Primary Examiner* — Tse Chen
*Assistant Examiner* — Jason Ip
(74) *Attorney, Agent, or Firm* — Marshall, Gerstein & Borun LLP

(57) ABSTRACT

A method, apparatus, and system display image data for a three-dimensional object in real-time, co-registering the image data acquired from a probe with the location on the three-dimensional object from which the image data was acquired, by tracking the position and orientation of the probe as the probe acquires the image data.

21 Claims, 30 Drawing Sheets

(56) References Cited

OTHER PUBLICATIONS

Ge, J., et al., "A Novel Optical Imager Towards Breast Cancer Diagnosis," *Medical Physics*, 33(6):1989 (Jun. 2006).

Godavarty, A. et al., "Fluorescence-Enhanced Optical Imaging of Large Phantoms Using Single and Simultaneous Dual Point Illumination Geometries," *Medical Physics*, 31(2):183-90 (Feb. 2004).

Jayachandran, B. et al., "Design and Development of a Hand-Held Optical Probe Toward Fluorescence Diagnostic Imaging", *Journal of Biomedical Optics*, 12(5):054014-1-10 (2007).

International Preliminary Report on Patentability and Written Opinion, PCT/US2007/079906, dated Mar. 31, 2009.

* cited by examiner

| Imaging Modality | Principle | Advantages | Disadvantages |
|---|---|---|---|
| X-ray | Uses x-rays of ~ 50 KeV photons to detect the x-rays attenuated by tissues of differing densities | Excellent resolution Good penetration depth | Ionizing radiation Poor contrast among soft tissues Overlooks 10% of breast cancer in non-calcified lesions |
| Computer Tomography (CT) | Uses x-rays at different angles for cross-sectional views | Same as x-ray technique, but provides more information | Greater exposure to x-ray radiation |
| Ultrasound (US) | Uses high frequency sound waves to detect the reflectance and transmittance from acoustically dissimilar tissues | Non-ionizing radiation Inexpensive Portable, safe, and versatile | Poor imaging quality Poor contrast |
| Magnetic resonance imaging (MRI) | Uses strong magnetic fields and RF waves to detect the emitted RF waves and relaxation of spin state of nuclei in tissues | Non-ionizing radiation Functional imaging Soft-tissue contrast Good resolution Good penetration depth | Strong magnetic field Expensive Not portable Slow process |

Figure 1

Sub-Surface Imaging

| NAME | BIT7 | BIT6 | BIT5 | BIT4 | BIT3 | BIT2 | BIT1 | BIT0 |
|---|---|---|---|---|---|---|---|---|
| BYTE 1 | 1 | FRI | OUT | P | S | L | M | R |
| BYTE 2 | 0 | X20 | X19 | X18 | X17 | X16 | X15 | X14 |
| BYTE 3 | 0 | X13 | X12 | X11 | X10 | X9 | X8 | X7 |
| BYTE 4 | 0 | X6 | X5 | X4 | X3 | X2 | X1 | X0 |
| BYTE 5 | 0 | Y20 | Y19 | Y18 | Y17 | Y16 | Y15 | Y14 |
| BYTE 6 | 0 | Y13 | Y12 | Y11 | Y10 | Y9 | Y8 | Y7 |
| BYTE 7 | 0 | Y6 | Y5 | Y4 | Y3 | Y2 | Y1 | Y0 |
| BYTE 8 | 0 | Z20 | Z19 | Z18 | Z17 | Z16 | Z15 | Z14 |
| BYTE 9 | 0 | Z13 | Z12 | Z11 | Z10 | Z9 | Z8 | Z7 |
| BYTE 10 | 0 | Z6 | Z5 | Z4 | Z3 | Z2 | Z1 | Z0 |
| BYTE 11 | 0 | PI13 | PI12 | PI11 | PI10 | PI9 | PI8 | PI7 |
| BYTE 12 | 0 | PI6 | PI5 | PI4 | PI3 | PI2 | PI1 | PI0 |
| BYTE 13 | 0 | YA13 | YA12 | YA11 | YA10 | YA9 | YA8 | YA7 |
| BYTE 14 | 0 | YA6 | YA5 | YA4 | YA3 | YA2 | YA1 | YA0 |
| BYTE 15 | 0 | RO13 | RO12 | RO11 | RO10 | RO9 | RO8 | RO7 |
| BYTE 16 | 0 | RO6 | RO5 | RO4 | RO3 | RO2 | RO1 | RO0 |

Figure 24

HAND-HELD OPTICAL PROBE BASED IMAGING SYSTEM WITH 3D TRACKING FACILITIES

RELATED APPLICATIONS

This application claims priority under 35 U.S.C. §119(e) to U.S. Provisional Application No. 61/118,326, filed Nov. 26, 2008, and by continuation-in-part under 35 U.S.C. §120 to U.S. patent application Ser. No. 12/442,505, filed Jun. 26, 2009, which is a National Stage of PCT/US07/79906, filed Sep. 28, 2007, which claims priority under 35 U.S.C. §119(e) to Provisional Application No. 60/847,812 filed Sep. 28, 2006.

BACKGROUND

Existing diagnostic imaging techniques of breast cancer include X-ray mammography, computer tomography (CT), ultrasound, magnetic resonance imaging (MRI), and nuclear imaging. FIG. 1 illustrates a table summarizing the advantages and disadvantages of each existing diagnostic imaging process or technique. These conventional techniques may be limited by poor resolution, use of harmful ionizing radiation, lack of portability, and/or expensive instrumentation.

Near-infrared (NIR) optical imaging is an emerging non-invasive technology that may be applied towards deep tissue imaging, with one application being breast cancer diagnostics However, the existing NIR optical imaging systems may be limited in a number of ways. For example, existing NIR imaging apparatus may be large and bulky systems, and thus, not generally portable. NIR imaging apparatus may also cause patient discomfort because the apparatus may require a patient to be placed in certain positions or may require compression of patient breast tissue. Moreover, conventional NIR imaging apparatus and methods may be limited to imaging only fixed volumes or certain shapes of breast tissue.

In recent years, hand-held based optical imaging systems have been developed for clinical applications of the imaging technology. These hand-held based systems represent an alternative to the conventional bulky optical imaging systems. However, the hand-held optical imagers available may be limited by having only flat measuring probe heads that cannot conform to different tissue curvatures and/or may not be capable of performing three-dimensional (3-D) tomography studies. In addition, all these optical imagers typically employ single point illumination (e.g., using only a single existing light source or multiple existing light sources in which only a single source is activated at one time) and single/multiple point detection measurement geometries that limit the total data acquisition rates in a clinical environment. Because of the relatively slow data capture rates, patient discomfort and wait time may be further increased.

SUMMARY

The disclosed method and system provides an optical imaging system and process that employs a flexible measuring probe head, simultaneous multiple point illumination and multiple point detection, and tracking facilities for co-registering location data with sensor data to enable generation of 3-D tomographic data for a target object (e.g., a tissue object or a phantom).

DRAWINGS

FIG. 1 illustrates a table of existing tumor diagnostic methods indicating principle of operation, advantages and disadvantages;

FIG. 24 depicts a set of data obtained from a tracking system operating in accordance with an embodiment of the presently described system;

DETAILED DESCRIPTION

Figure 2:
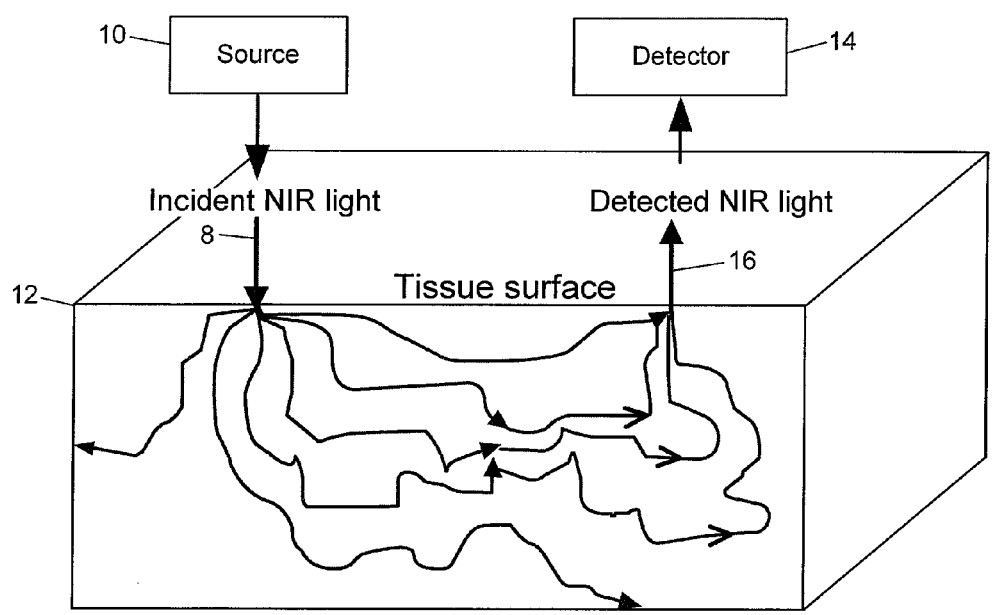
FIG. 2 illustrates a general optical imaging process.

FIG. 2 illustrates general principles behind an optical imaging process. Light 8 from a source 10 is projected on a target tissue 12 at a wavelength of 700-900 nm. The tissue 12 may minimally absorb the light 8 while reflecting and scattering a majority of the light. A corresponding light detector 14 may be positioned to measure characteristics of the reflected light 16, such as intensity, phase, or time delay.

Generally, when NIR light is launched onto a tissue surface, light propagates into the tissue and is minimally absorbed (in biological tissues, hemoglobin and water are least absorbent in the near-infrared spectrum) and preferentially scattered, allowing deep penetration of the light into the tissue and providing an opportunity for diagnostic imaging. The reflected light and/or trans-illuminated light (i.e., light that enters tissue at a first surface and exits the tissue at a second surface opposite the first surface) may be collected at a set of point locations on the tissue surface. From the collected reflected or trans-illuminated measurements, images of scattering ($\mu s$) and absorption ($\mu a$) coefficients of the entire tissue domain may be generated using appropriate light propagation models and reconstruction algorithms (discussed further below). Diffuse optical imaging enables researchers to translate the highly scattered light signals into clinically meaningful information about human tissue. For example, optical properties may be used to locate and identify physiological changes in the tissue that may indicate the existence and/or location of tumors.

Figure 3:
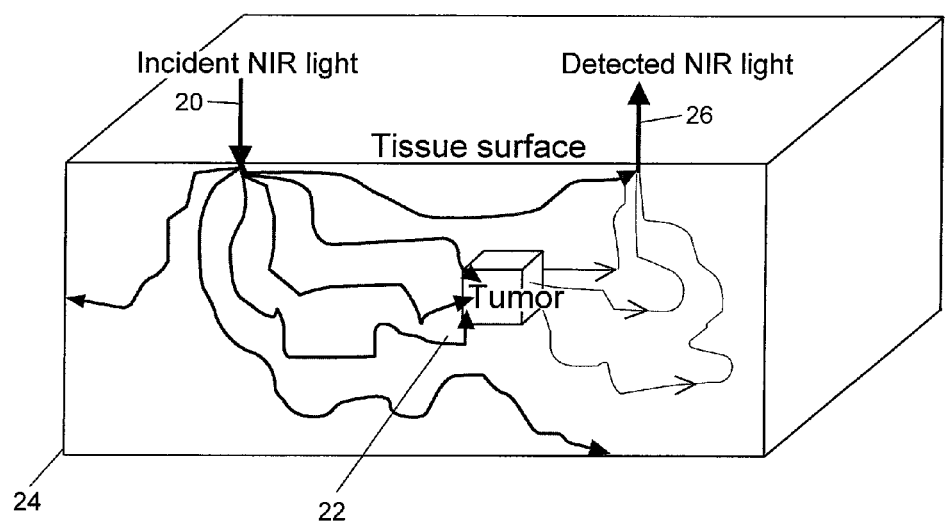
FIG. 3 illustrates a general optical imaging process in tumor detection.

Differences in composition of the tissue may cause a difference in the light characteristics (e.g., in terms of reflected/trans-illuminated light intensity, phase, time delay, etc.) of the imaging data collected. This difference in light characteristics may be used to determine abnormal tissue growth. For example, optical imaging may be used to detect a breast tumor in a chemical environment by looking for two intrinsic cancer signatures: increased blood flow (as shown by the total hemoglobin concentration) and hypermetabolism (as shown by a drop in oxygen concentration). As illustrated in FIG. 3, when NIR light 20 encounters an angiogenic (growth of blood vessels from surrounding tissue to solid tumors) region 22 of a breast tissue 24, light may be absorbed based on the different concentrations of hemoglobin in that area of the breast, thus providing endogenous contrast between normal and tumor tissue. The difference in light characteristics of the collected diffused light 26 may reflect the difference in absorption and/or scattering arising from this angiogenic region 22.

To detect lesions smaller than about 0.5 cm (in diameter) external contrast agents may need to be used in order to improve the optical contrast between normal and diseased tissues in a process known as fluorescence enhanced optical imaging. Fluorescence-enhanced optical imaging involves the administration of exogenous fluorescent contrast agents that specifically bind to target tissue (e.g., tumor tissue) and that are excitable in the NIR wavelength range. The external fluorescent contrast agents molecularly target the metastatic cancer cells within the breast tissue and enhance the optical contrast between the cancerous cells and the background breast tissue.

Figure 4:
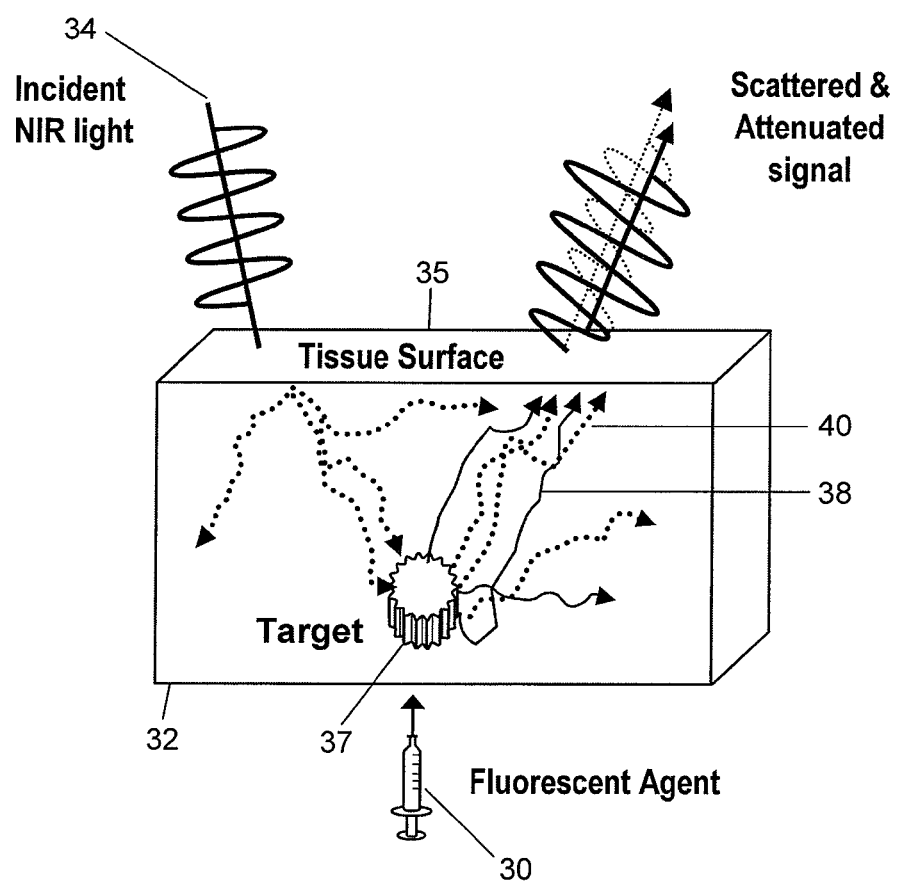
FIG. 4 illustrates a fluorescence enhanced optical imaging process.

FIG. 4 illustrates a fluorescence enhanced optical imaging process. In a fluorescence-enhanced optical imaging process, a target-specific florescent contrast agent 30 may be injected into the tissue 32. When NIR light 34 (having a wavelength of 700-900 nm) is launched at the tissue surface 35, the minimally-absorbed and preferentially-scattered excitation photons propagate deep into the tissue 32. Upon encountering a fluorescent molecule 37 (e.g., found at the site of target tissue substructure), the photons excite the fluorescent molecule 37 from its ground state to a higher orbital level. After residing at the higher energy orbital for a period (known as the fluorescence lifetime), the fluorescent molecule emits a fluorescent signal 38 at a greater wavelength than the incident NIR light 34. The emitted fluorescent signal 38 along with the attenuated excitation signal 40 (which is at the same wavelength as the incident light) propagates back through the tissue surface where it is detected. At a detection site (not shown in FIG. 4), appropriate optical filters may be used to separate the fluorescence signal from the attenuated excitation signal to provide relevant light characteristic data.

Imaging Data Signal Processing

Three distinct measurement techniques may be used to process the collected light characteristic data in optical imaging. These techniques include continuous wave, time-domain (TD), and frequency-domain (FD) based imaging. Each of these measurement techniques has advantages and disadvantages, and the selection of the appropriate technique largely depends on the specific application and requirement.

Continuous wave measurement technique uses steady state light of constant intensity on the tissue surface and measures the attenuated intensity of the trans-illuminated and/or reflected light. In continuous wave based fluorescent optical imaging the NIR light attenuates due to absorption and scattering in the tissue medium. Upon encountering the florescent molecule, a steady state florescent signal is emitted, which attenuates before it is detected at the tissue surface. Continuous wave-based imaging instrumentation is relatively simple and involves low-cost optical components. The major disadvantages of continuous wave measurement technique include difficulty in resolving tissue absorption from scattering and inability to image the fluorescence decay kinetics. When independent measurements of tissue optical properties (i.e. absorption, scattering or fluorescence lifetime) and/or depth information are required, the use of TD or FD measurement techniques may be necessary.

Time domain (TD) measurement techniques illuminate tissue with ultra fast (e.g., in the femtosecond to picosecond time range) photon pulses and resolve the arrival of the photons as a function of time at different locations around the tissue boundary. In a TD-based fluorescence optical imaging process the excitation light pulse broadens and attenuates as it travels through the scattering medium. Upon encountering a fluorescent molecule, a fluorescent light pulse is emitted, which broadens and attenuates as it propagates in the tissue medium. This broadened pulse of fluorescent light is further broadened and attenuated due to absorption and scattering in the tissue medium, before it is detected at the tissue surface using, for example, fluorescence optical imaging.

The TD measurement technique may provide better depth information compared to a continuous wave measurement technique. Although TD based measurements provide a wealth of information that may be used to map optical properties of tissues, TD measurement techniques may be limited by their large signal-to-noise ratio (SNR) range, which may require significant data acquisition times compared to CW and FD measurement techniques.

In FD-based fluorescence optical imaging, modulated excitation light is launched onto the tissue surface and the modulated fluorescent signal is detected at the tissue surface in terms of amplitude and phase shift. Measurements of the light intensity and the phase shift of the photon wave-front are obtained with respect to the source light information about the tissue optical properties and fluorochrome distribution. Frequency domain measurement technique may be preferable over TD measurement technique due to its inexpensive instrumentation. In addition, the steady-state FD measurements in terms of amplitude and phase shift are minimally corrupted by ambient light, since the instrument detects only a modulated signal. Thus, the FD instrument automatically acts as a filter for ambient light rejection, which is an advantage of FD measurement techniques over continuous wave or TD measurement techniques. However, FD measurement techniques require frequencies of several hundred MHz or higher to achieve depth information that may be difficult to obtain using continuous wave technique. In practice, usually a single frequency may be employed, and the phase shift may be used to estimate the mean time of flight of the photons. However, data obtained at multiple frequencies may improve FD imaging performance and may be equivalent to TD data via the inverse Fourier Transform.

Source and Detector Configurations for Optical Imaging

NIR based imaging approaches, whether based on endogenous or exogenous contrast, involve trans-illumination and/or reflection measurements. These measurements represent the light propagation between light sources and detector sensor pairs, and are based on excitation illumination and excitation/emission detection. Generally, trans-illumination is the shining of a light through a target tissue, such as breast tissue, to observe the absorption pattern from the opposite side of the tissue medium. Reflection measurements involve observing light reflected off a tissue surface from the same side as the incident light.

Generally, existing optical imaging configurations for arranging sources (for providing incident/excitation signals) and detectors (for collecting reflected and/or trans-illuminated NIR signals, fluorescence or non-fluorescence signals) may be broadly categorized into projection shadow, circular, and sub-surface/reflective configurations.

Figure 5:
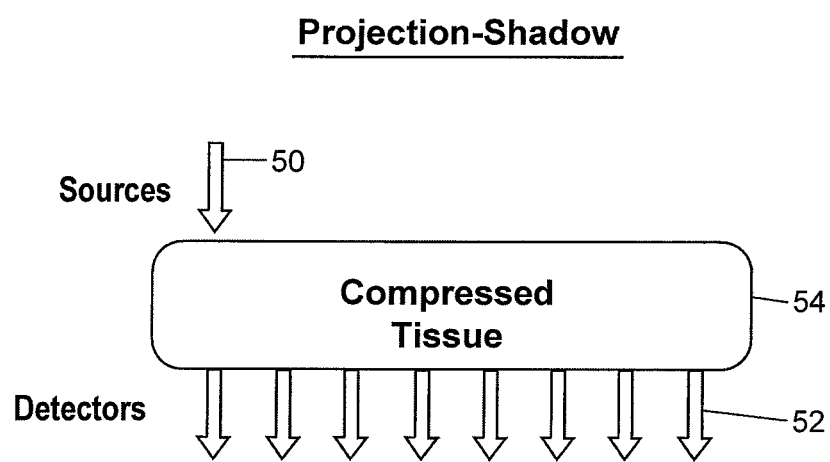
FIG. 5 illustrates a projection-shadow optical imaging process.

FIG. 5 illustrates a projection-shadow optical imaging process. Projection-shadow imaging involves collecting trans-illuminated light from the tissue object. Trans-illuminated light may refer to light that traverses a surface(s) of a tissue. In trans-illumination method, sources 50 and detectors 52 are placed on opposite sides of breast tissue 54. In this geometry, single/multiple sources may be deployed on an opposite plane that is parallel to the detector plane that has single/multiple detectors. Optical properties of the three dimensional tissue are obtained between the source and the detector planes. This method generally requires compression of the target tissue. The compressed tissue configuration may be analogous to x-ray mammography, and may be disadvantageous due to patient discomfort caused by tissue compression and due to limited information obtained for the entire breast tissue.

Figure 6:
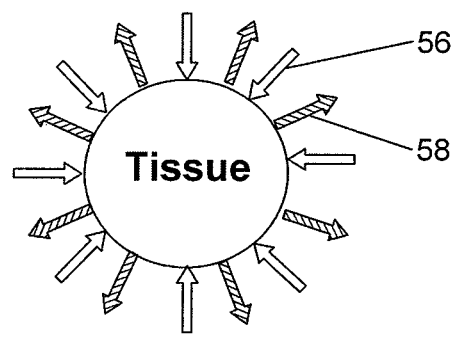
FIG. 6 illustrates a circular imaging process.

FIG. 6 illustrates a circular imaging process, wherein both the reflected and trans-illuminated light is collected along a circular circumference of the tissue. In this configuration, multiple sources 56 and detectors 58 are disposed about the circular circumference of the tissue. The circular configuration may be minimally discomforting to a patient, but is limited by the bulky and non-portable size of the apparatus.

Figure 7:
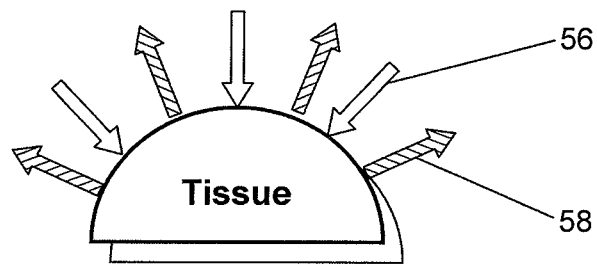
FIG. 7 illustrates general sub-surface imaging.

FIG. 7 illustrates sub-surface imaging, which may involve collecting reflected and/or trans-illuminated light using multiple sources 56 and detectors 58. This configuration requires no tissue compression, and may be designed to mimic a hand-held imaging probe. To date, all the optical imaging systems and hand-held probes developed using the sub-surface imaging configuration are designed to only collect reflected light using flat measurement probe heads.

Three-dimensional tomography studies may be performed using the projection-shadow or the circular imaging configuration. However, 3-D tomography studies have been limited by the sub-surface configuration because of the limited depth information obtainable in the absence of trans-illuminated measurements, and also from lack of co-registering the source and detector locations on the target tissue object that is imaged.

Illumination Area

Figure 8B:
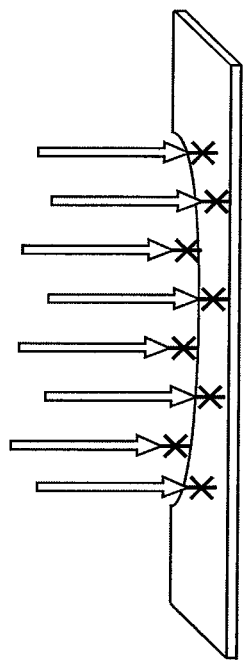
FIG. 8B illustrates a wide-area illumination.
Figure 8A:
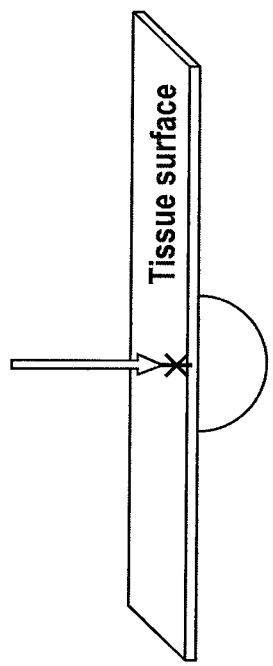
FIG. 8A illustrates a point-wise illumination.

There are essentially two methods of illuminating the tissue surface; wide-area illumination as illustrated in FIG. 8B and point-wise illumination as illustrated in FIG. 8A. In wide-area illumination the intensity is typically not uniform (e.g., the intensity may typically be relatively higher at the center than at the edges of the region). To date, most optical imaging studies have typically been performed using sequential single point illumination (FIG. 8A) and sequential or simultaneous multiple point detection measurement techniques. Although the data acquisition rates are enhanced upon using simultaneous point detection techniques, in terms of illumination geometries, most optical imaging studies have been limited to using sequential single point illumination of the tissue surface during imaging. For sub-surface optical imaging, a point illumination system vastly reduces variations in intensity on the imaging surface overcoming one of the limitations posed by wide area illumination as shown in FIG. 8B. However, illumination by excitation light from a single point interrogates a relatively small portion of tissue volume 8A, thus increasing the total data acquisition times in order to image the entire tissue volume. In addition, sequential single point illumination may also provide insufficient light intensity to perform tomographic studies on large tissue volumes with greater penetration depth (since optical signals decay exponentially with distance). Weak optical signals are usually dominated by noise, thus impacting the measurement precision and accuracy, and eventually hindering the accurate reconstruction of the target location and size. Thus, sequential single point illumination not only may impact the total imaging time (due to small portion of tissue volume illumination), but may also be insufficient to generate a detectable NIR signal from small and/or deeply located targets.

The imaging method and system embodiments described herein use various combinations of source-detector configuration, illumination, and signal processing to provide an improved hand-held optical imaging probe that may be used for 3-D tomography studies, with reduced total imaging time, and ability to image any tissue curvature.

Probe Head

Figure 9A:
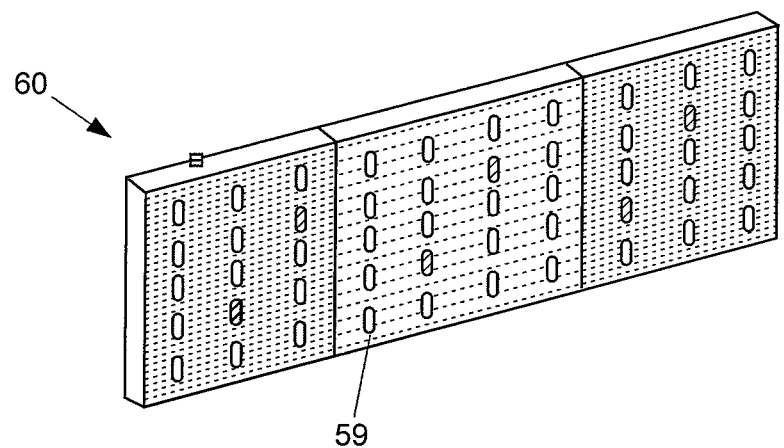
FIG. 9A illustrates a support plate that may be used in a probe head.

FIG. 9A illustrates a support plate 60 that may be used in an embodiment of an improved NIR imaging apparatus and method to arrange a plurality of fiber optic cables (the term fiber optic cable(s) is used interchangeably with optical fiber cable(s) herein). In particular, first ends 59 of fiber optic cables may be terminated on the support plate 60 in a direction transverse the plane of the support plate 60. In this embodiment, some optical fibers may be used as optical source fibers to carry light from a light source to a terminal end at the plane of the support plate or as optical detector fibers that receive and collect light at the plane of the support plate and channel the received light along their lengths to a detector or a plurality of detectors.

Figure 10A:
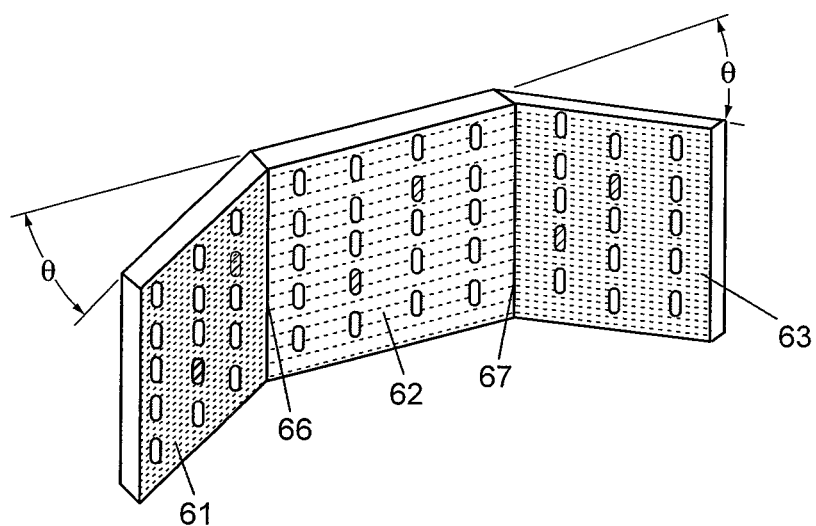
FIG. 10A illustrates a support plate having a plurality of pivotable plate sections.
Figure 10B:
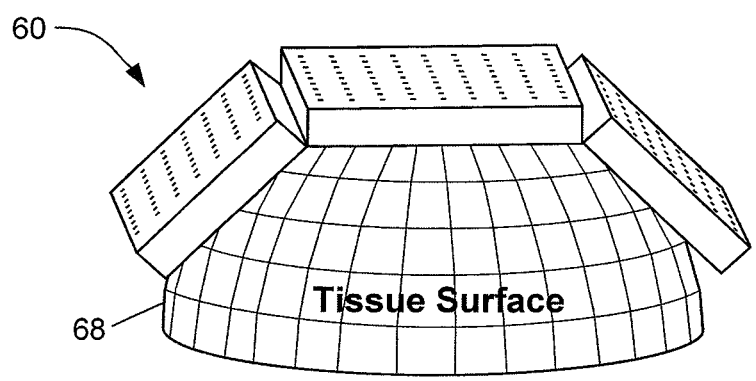
FIG. 10B illustrates the support plate of FIG. 10A on a tissue surface.

FIG. 10A illustrates that the support plate 60 may be divided into three planar sections or plate sections 61, 62, 63. The planar sections 61-63 may be pivotably coupled to one another. In the embodiment of FIG. 10, the first plate section 61 may be pivotably coupled at an edge 66 with the second plate section 62. The second plate 62 may be pivotably coupled to the third plate 63 at another edge 67 of the second plate 62. In this embodiment, the support plate 60 may be conformed, along the pivotable edges 66 and 67, to a surface 68 of a three-dimensional target object, such as a breast tissue or any other body part, as illustrated in FIG. 10B. This curved geometry of the optical probe embodiment enables improved contact of the source-detector array on a three-dimensional object and thus provides greater accuracy on the tissue data collected.

Figure 11:
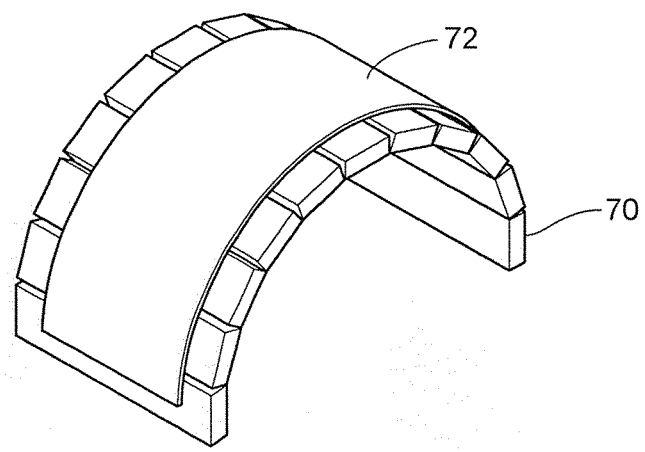
FIG. 11 illustrates another embodiment of a support plate comprising a plurality of plate sections.

FIG. 11 illustrates another embodiment where the support plate 60 may be divided into a plurality of plate sections 70 that may be connected together by pivotably coupling along their edges, or by using any flexible sheet of material 72, such as an aluminum or other appropriate material. In this manner, a greater amount of surface contact to the target object may be provided based on the plurality of discrete sectional plates 70. Alternately, a flexible sheet of material (or combination of materials) without any plurality of sectional plates can be used directly, upon which the first ends of the optical fiber cables can be connected at various locations via drilled holes.

Figure 12:
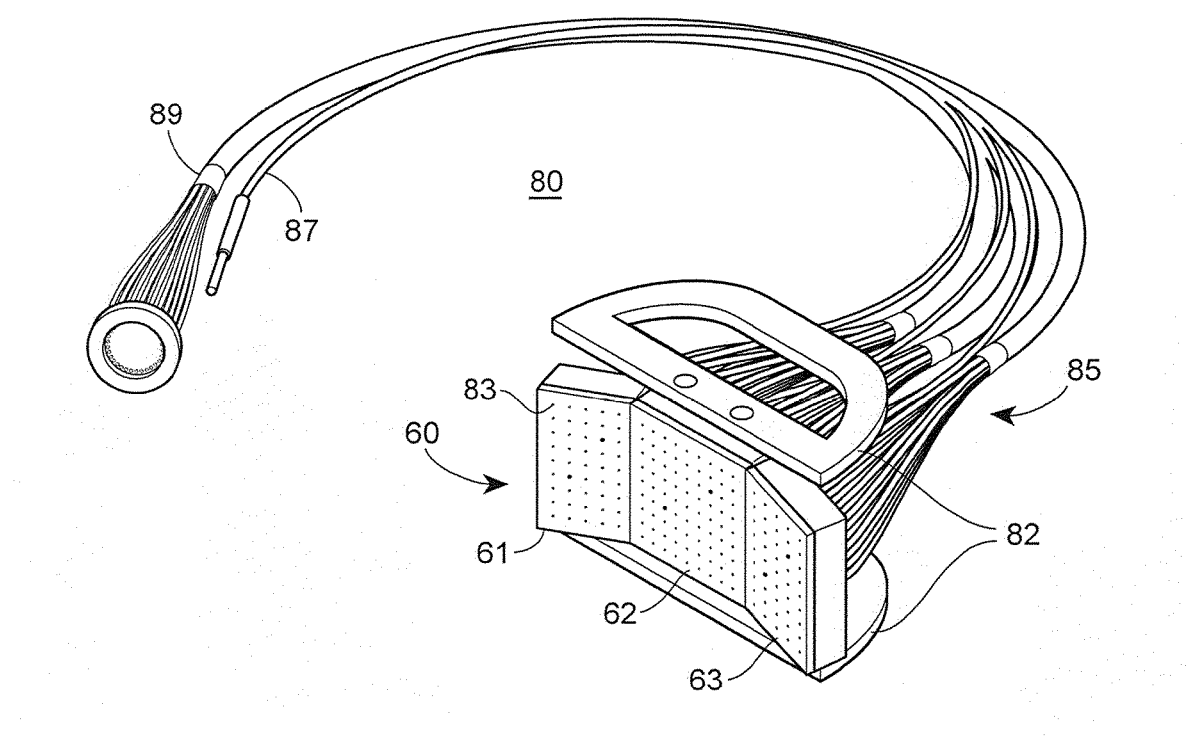
FIG. 12 illustrates an optical imaging probe using the support plate of FIGS. 10A and 10B.

FIG. 12 illustrates an optical imaging probe 80 using the support plate 60 of FIGS. 10A and 10B. The support plate 60 having planar sections 61-63 may be coupled to a support frame 82. First ends 83 of optical fibers 85 (including optical source fibers and optical detector fibers) may be terminated at the support plate 60. Optical source fibers may be arranged in a first bundle 87 for coupling to a light source. Optical detector fibers may be arranged in a second bundle 89 for coupling to a detection system or detection module.

Figure 9B:
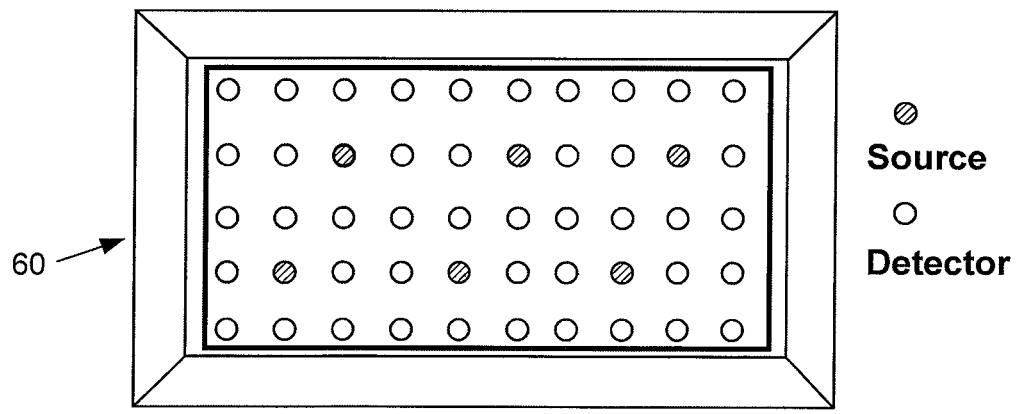
FIG. 9B illustrates a detailed view of the support plate for FIG. 9A.

In some embodiments, simultaneous multiple point illumination and simultaneous multiple point detection technique using optical fibers may be used. Using the support plate 60 of FIG. 9A, where the face of plate is enlarged in FIG. 9B, a plurality of optical source fibers ends may be disposed on the plate 60 at locations indicated by dark circles. Ends of optical detector fibers may be terminated at the plate and positioned around the optical source fibers ends as indicated by light circles in FIG. 9B. The optical detector fibers may receive and collect light at the plane of the support plate and channel the received light along their lengths to a detector or a plurality of detectors.

In some embodiments, each of the optical source fibers may be adapted to simultaneously launch the NIR light from a light source onto the tissue object surface. In some embodiments, each of the optical source fibers may sequentially emit NIR light from a light source onto the tissue object surface. Moreover, the light may be emitted from each of the optical source fibers at substantially the same intensity (preferably) or even different intensities. In some embodiments, the intensity difference between any one of a set of optical source fibers disposed on the planar support frame may be within three percent (sometimes higher depending on the application). If the simultaneous light intensities are significantly different, they may be accounted for in mathematical models representing light propagation in tomography related studies.

Figure 13:
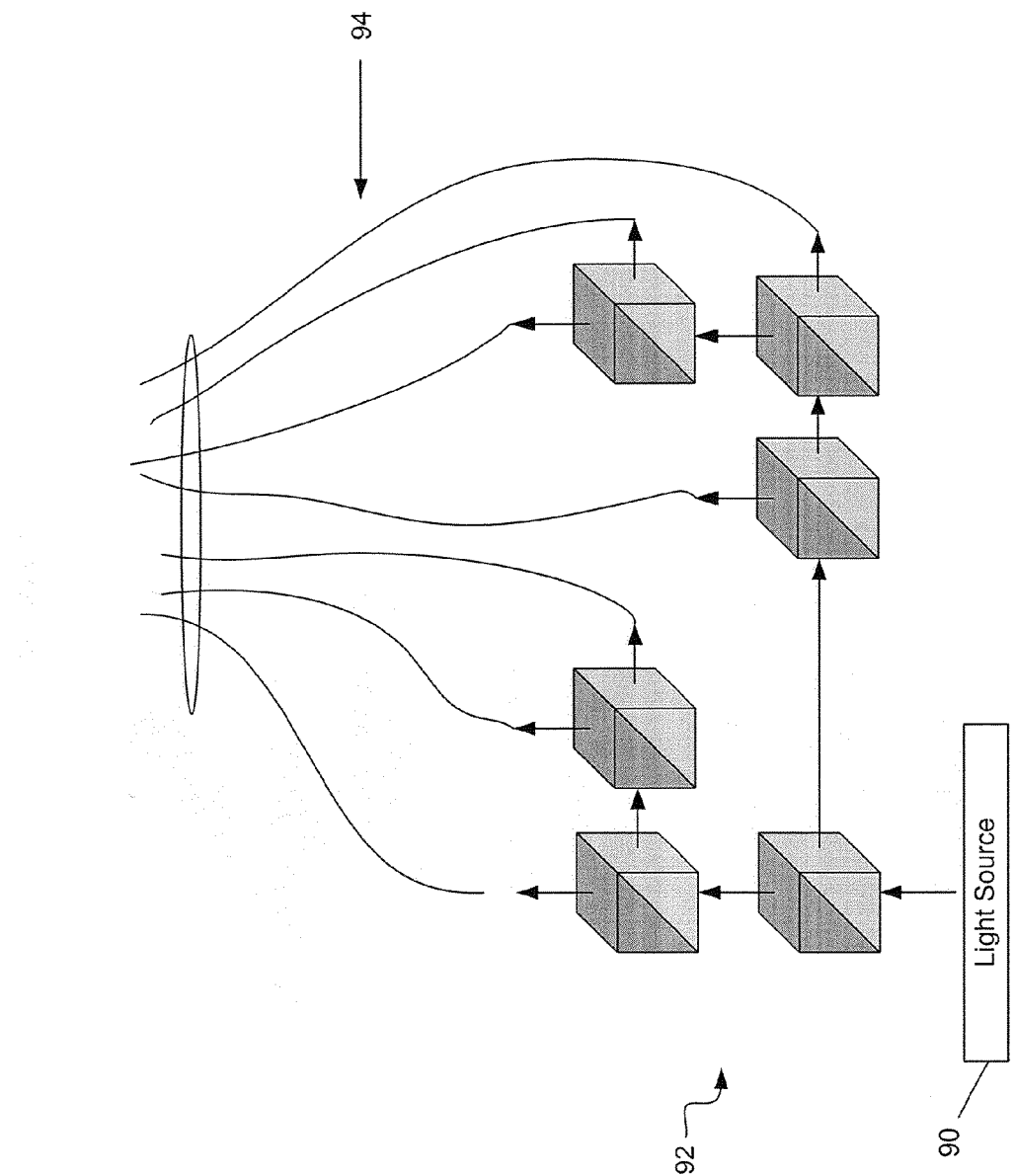
FIG. 13 illustrates an embodiment of a system using optical dividers to simultaneously illuminate a plurality of optical source fibers.

FIG. 13 illustrates an embodiment of a system for simultaneously emitting a plurality of simultaneous light beams at the support plate at substantially the same intensity via a set of optical source fibers. In this embodiment, a light source 90 may be used to generate light that is applied to a plurality of optical dividers 92. In some embodiments, the light source 90 may be a laser. In other embodiments, the light source 90 may be any suitable light source for producing a beam of light at necessary intensities. The optical dividers 92 may be prisms that are aligned in a manner to provide the substantially equal or unequal (but pre-determined) beams of light. In some embodiments, this may require aligning the prisms to provide a total variance in light intensity between the beams of less than about three percent. The plurality of light beams resulting from the optical division may be channeled into ends of a plurality of optical source fibers 94. The second ends of the plurality of optical source fibers 94 may then terminate at the support plate 60 described above (e.g., ends 83 as illustrated in FIG. 12).

Figure 14:
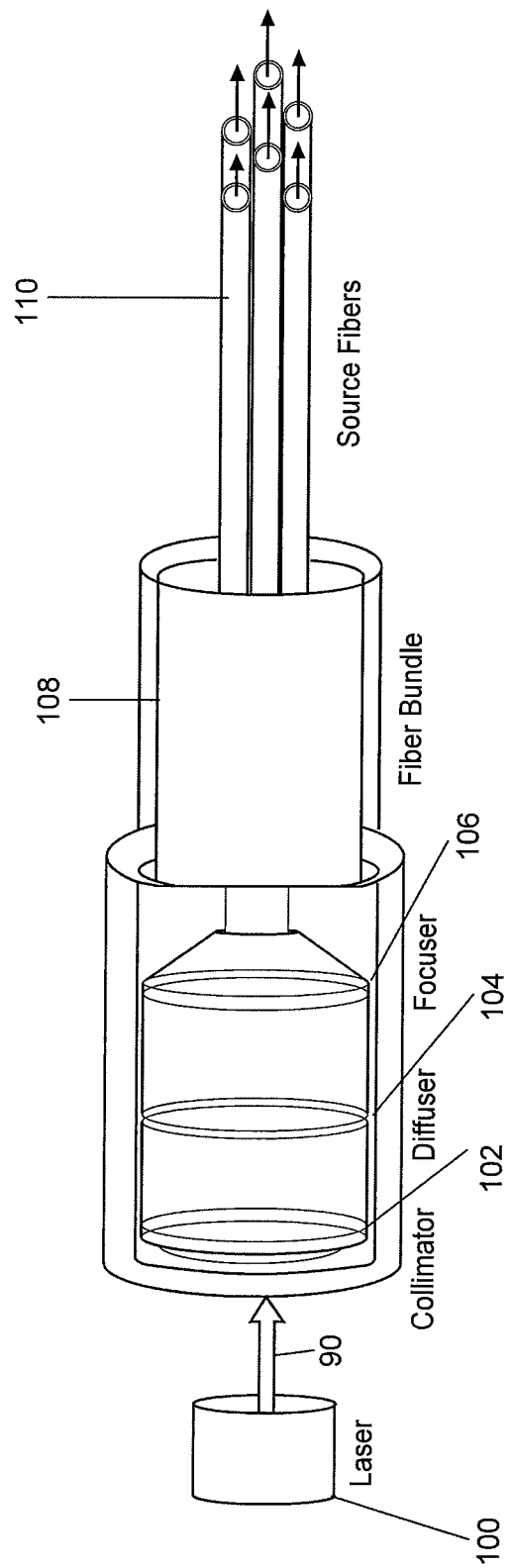
FIG. 14 illustrates an embodiment of a system that provides a plurality of light sources using different optical source lenses.

FIG. 14 illustrates another embodiment of a system for simultaneously emitting a plurality of light beams at the support plate 60 at substantially the same intensity via the set of optical source fibers. In this embodiment, a laser 100 may be used as a light source (although other light sources for providing light to the system may be used). The laser light may be collimated at a collimator 102. In some embodiments, the collimator 102 may be optional. Collimated light output from the collimator 102 may then be channeled to a diffuser 104 for evenly spreading the collimated light over a particular surface area. In this embodiment, the diffuser 104 spreads the collimated light over the input surface of a focuser 106. The focuser 106 may be selected to concentrate collimated light onto first ends of a bundle 108 of optical source fibers. In some embodiments the diffuser 104 and/or focuser 106 may be optional. The optical source fibers 110 may then terminate at seconds ends at the support plate 60 (e.g., ends 83 as illustrated in FIG. 12).

Sensor and Detector System

Figure 15:
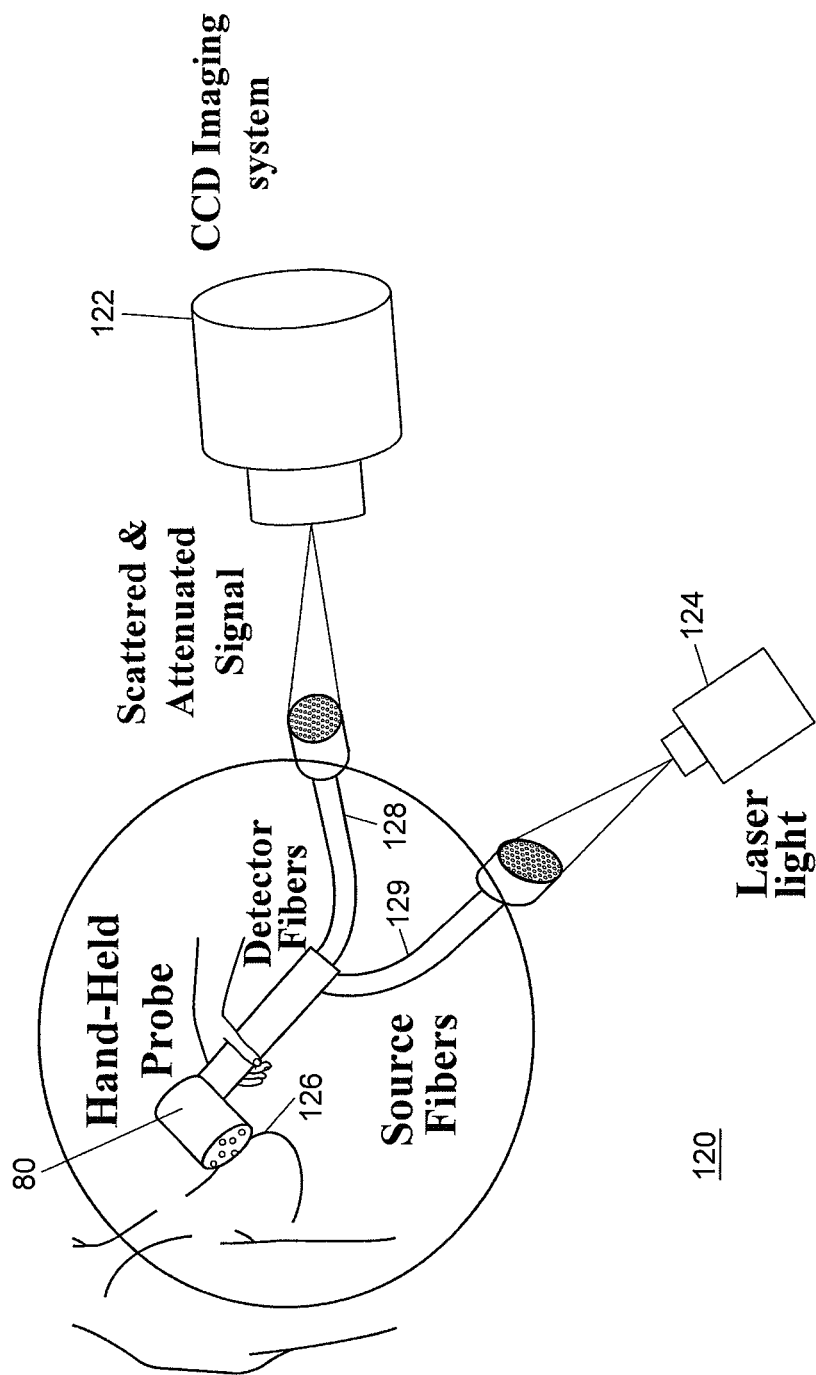
FIG. 15 illustrates a optical imaging system embodiment using the probe of FIG. 12.

FIG. 15 illustrates an optical imaging system 120 embodiment using the probe 80. In this embodiment, a fluorescence-enhanced or non-fluorescence diffuse optical imaging process may be used. A frequency-domain intensified CCD (ICCD) detection module 122 may be coupled to the hand-held optical probe 80. The detection module 122 may be any CCD sensor or other detector such as photo-multiplier tubes (PMT), avalanche photo diodes (APD), or silicon photo diodes. These detectors may be used individually or in a plurality to detect light. If a plurality of the detectors is used, the detectors may be activated sequentially or simultaneously. The detection module 122 may be configured to operate as a time-dependent (FD or TD) and/or as a time-independent (CW) detection system. The detector system may operate in conjunction with a light source 124 using TD, FD, or CW approaches. While FIG. 15 illustrates that the light source 124 is a laser source, any other light source capable of providing the appropriate light characteristics may be used. As illustrated in FIG. 15, light from light source 124 may be projected on to a target tissue surface 126 via optical source fibers 129. The hand-held probe 80 may collect NIR signals from different points on the tissue boundary surface 126 via optical detector fibers 128, where the signals may be simultaneously processed using the gain-modulated ICCD detector 122 for an enhanced data acquisition rate. A homodyne technique may be implemented in the system 120 where the laser source 124 and the detector 122 are modified at the same frequency (e.g., in the MHz range). Data acquisition rates of the homodyned frequency domain measurements may depend on the number of phase delays between the frequency synthesizers modulating the image intensifier and the laser diode modulation, the number of repeated images averaged to acquire phase-sensitive images, the integration or exposure time of the CCD to obtain each image, and the degree of data binning downwards from a pixelated image in the CCD. The combination of the above variables may be assessed to determine the data acquisition scheme with minimal measurement time, reduced measurement errors, and maximum resolution of the optical images. In some embodiments, the frequency-domain measurements detected by the detection module 122 may be based on the heterodyne technique, where the modulation frequencies at the laser source 124 and the detector 122 are not the same.

Figure 16:
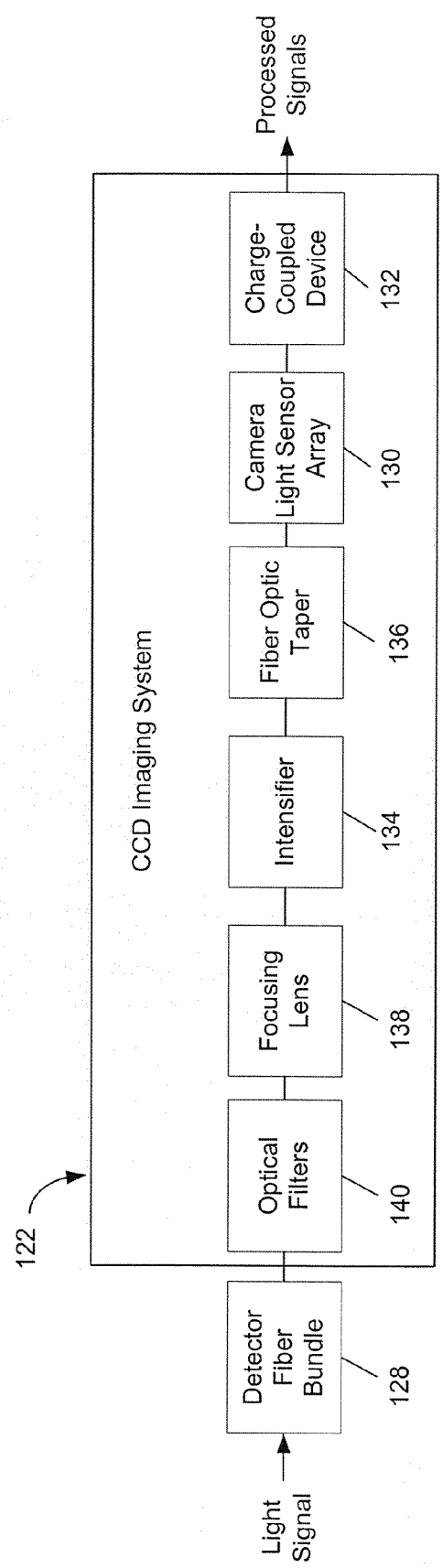
FIG. 16 illustrates a detection system using a charge-coupled device.

FIG. 16 illustrates further details of the CCD imaging module or system 122. The CCD imaging system 122 may be built using a custom 16-bit CCD camera that includes a photo-detector array 130 for transforming light signals into corresponding electrical signals and a charged-coupled device (CCD) 132 for processing the electrical signals. The photo-detector array 130 and charge-coupled device 132 may enable higher frame transfer capability to enhance image acquisition and storage rates. The photo-detector array 130 may be fiber optically coupled to a near infrared (NIR) sensitive image intensifier 134 via a fiber optic taper 136. The image intensifier 134 may be included in the CCD system to amplify weak light signals at MHz range. The NIR-sensitive image intensifier 134 (e.g., a conventional filmed or filmless tube) may generally work to reduce image retention effect and to increase sensitivity to weak NIR (both fluorescence and non-fluorescence) signals. A custom-built fiber optic taper 136 may be used to interface the output of the intensifier to the photo-detector array 130 to improve the coupling efficiency of image intensifier. In the absence of an image intensifier, it is not possible to implement a frequency-domain analysis because the image intensifier allows the signal from the CCD camera to be modulated.

The optical detector fibers in bundle 128 may be coupled to optical filters 140 and a focusing lens 138, where the focusing lens 138 then outputs light signals to the intensifier 134. Different optical filter combinations (e.g., interference, long pass, band pass, holographic, etc.) may be used to isolate and extract light signals at particular wavelengths of interest and to remove signals at other wavelengths. In the case of fluorescence-enhanced optical imaging, use of an appropriate optical filter combination may help minimize the excitation leakage that prevents the detection of weak and low intensity fluorescence signals arising from deep and/or small targets.

Co-Registration of Sensor Data with Location Data

In both modeling and image reconstruction, a region of interest(s) (e.g. 2-D or 3-D tissue object or phantom) may be divided into discrete 2-D or 3-D elements. Due to the limited surface area of the probe head, sensor data are captured only for a portion of the region of interest at one time. To obtain three-dimensional visualization of a large region of interest, each time the probe is moved, its position and orientation may be monitored and co-registered or mapped. As used herein, co-registration refers to the mapping of sensor data for a particular region onto to a map (e.g., a discretized mesh) of the entire region of interest(s). Generally, registration provides 3-D location and orientation data for the sensor data. For example sensor data captured during a first period at a first position of the probe may be mapped to a corresponding first position of a map of the entire region of interest. To implement self-registration or co-registration of the sensor data for the region of interest, an ultrasonic tracking system may be used to monitor the location of the probe.

Acoustic trackers that determine probe location via sound may be appropriate for an optical imaging system because acoustic receivers may be small, lightweight, and inexpensive. Moreover, unlike magnetic trackers, acoustic trackers may not suffer from distortion in the presence of magnetic fields and may not require specially designed environment for operation. In some embodiments, the optical imaging probe 80 of FIGS. 12 and 15 may incorporate a 3-D tracking device that uses acoustic signals to monitor the 3-D position and orientation of the optical imaging probe.

Figure 17:
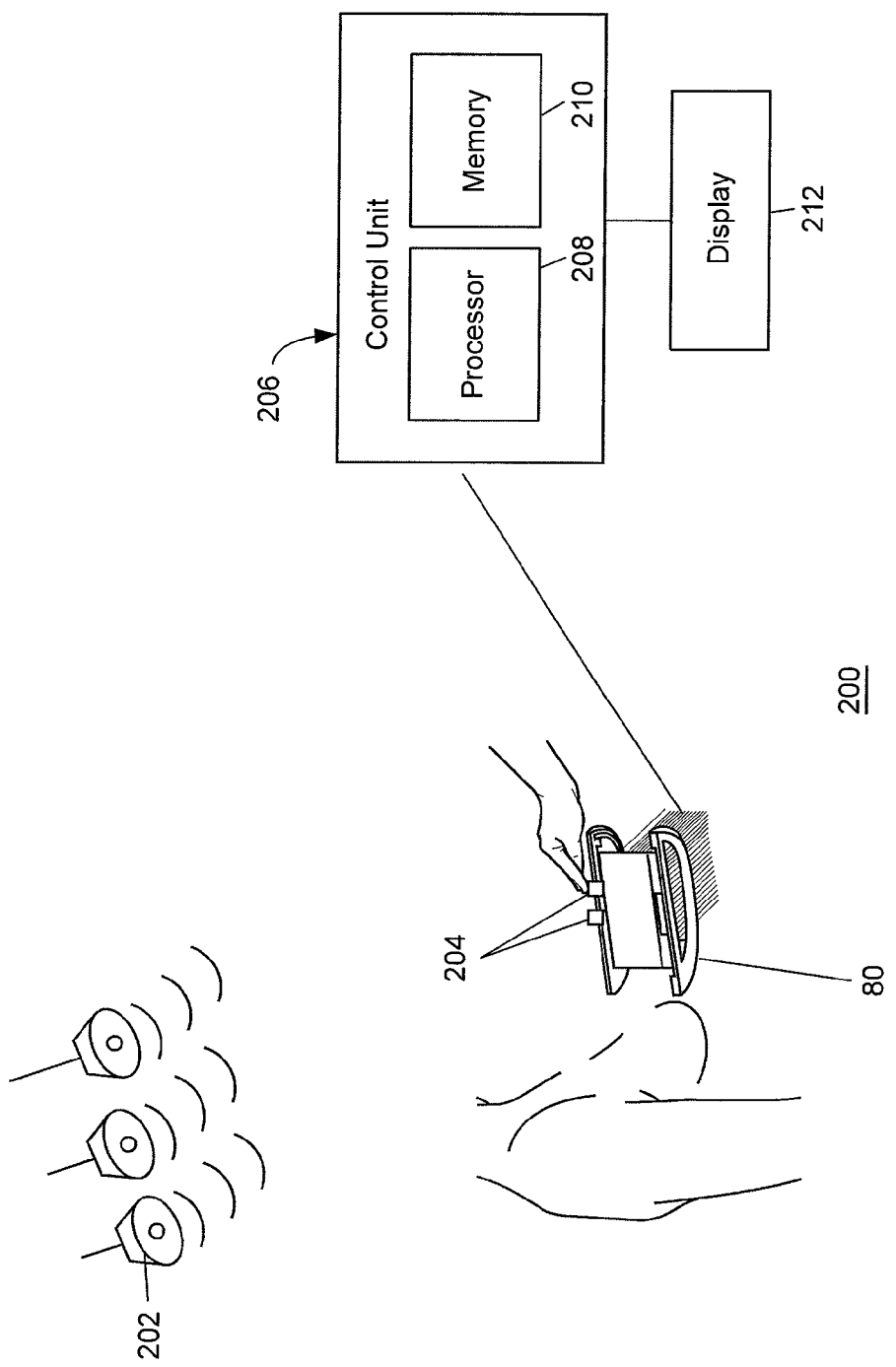
FIG. 17 illustrates an ultrasonic tracking system that may be used in conjunction with an optical imaging probe.

FIG. 17 illustrates an ultrasonic tracking system 200 that may be used in conjunction with the optical imaging probe 80 described above. The tracking system 200 may comprise a set of transmitters 202, a set of receivers 204 coupled to the optical imaging probe 80, and a control unit or processing unit 206. The processing unit 206 may be a computing device having a processor 208 and a memory 210, as known by those skilled in the art. The processing unit 206 may be coupled to a display device 212 for displaying images. In the embodiment illustrated in FIG. 17, the set of transmitters 202 may be located at a fixed location with respect to the receivers that are coupled to the imaging probe. In an alternative embodiment, the transmitters may be coupled to the imaging probe while the receivers may be placed at a fixed location with respect to the transmitters.

The set of transmitters 202 of FIG. 17 may comprise several speakers that send acoustic signals (e.g., in the ultrasonic range) to the receiver 204. The set of receivers 204 may be coupled to the hand-held probe 80 by, for example, embedding several microphones on the surface of the hand-held probe 80. The microphones may sample signals from the set of transmitters at a constant rate. The control unit 206 may decode signals from receivers in the following manner.

The speakers 202 may emit ultrasonic pulses at regular intervals. The receivers 204 may detect the pulses and record their times of arrival and from that information, the computing device 206 may be used to determine the position of the hand-held probe with respect to the fixed transmitter location. Because the times of transmission of the pulses are known, the times of flight of the pulses may be computed. This flight time may then be used to compute the distances between the speaker and sensor by multiplying the times of flight by the speed of sound in air. These distances and the known positions of speakers may provide sufficient information for computing the position and orientation of the hand-held probe.

Figure 18:
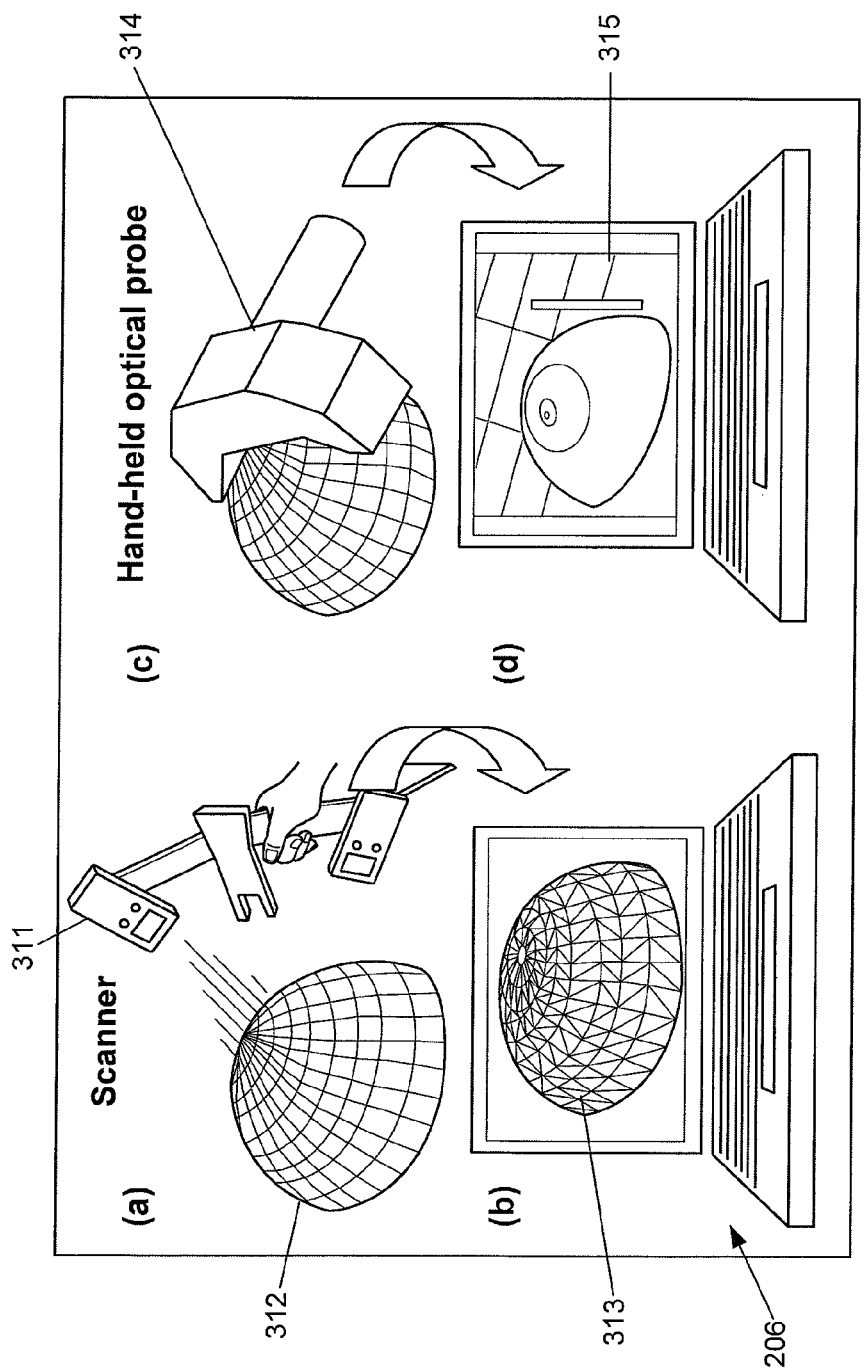
FIG. 18 illustrates a process embodiment of an optical imaging system.

FIG. 18 illustrates a possible embodiment of the process of obtaining 3-D tomography-relevant sensor data using a self-registering (automatic registering) hand-held probe based imaging system. A three-dimensional optical scanner 311, as known in the art, may be used on the target object 312 (without any contact) to provide a 3-D surface image of the target object, which can be volume rendered and discretized using appropriate meshing software, as known in the art. In some embodiments, the volume rendering process may involve generating a three-dimensional (3-D) mesh of point coordinates or point locations sub-surface to the rendered 3-D surface image (e.g., for the entire volume of the target object 312). This 3-D mesh may be known as a "phantom mesh"

because it serves as a structure over which the target data may be mapped or overlaid or with which the target data may be co-registered. The 3-D mesh of the target object 313 may be displayed on computing device 206. A probe 314 for collecting sensor data, such as the optical imaging probe described above, may then be traced over the target object 312 to obtain sensor data. The 3-D location map of the probe 314 with respect to the 3-D mesh of the target object 313 may be obtained using the tracking system 200. In some embodiments, the computing system 206 may be programmed (e.g., using appropriate software and algorithms, such as those described below) to receive sensor data from the probe for a time period, receive probe position data from the tracking system 200 for the time period, and co-register the sensor data with appropriate mesh locations on the 3-D mesh based on the position data. In this manner, the location data and the sensor data collected over a region may be mapped to the corresponding region on the 3-D mesh surface 313 to generate co-registered map sensor data 315. The computing device 206 may co-register or map sensor data with respect to a reference position arbitrarily chosen on the 3-D mesh of the target object 313. The computing system 206 may be further programmed to process the sensor data before and/or after mapping/co-registering to the mesh depending on a particular application of the sensor data. This co-registered sensor data may then be transformed into a 2-D and/or 3-D tomogram using appropriate algorithms. These tomograms may include reconstructions of subsurface structures within the target object. The subsurface structures may include abnormal tissue such as tumors.

Figure 19:
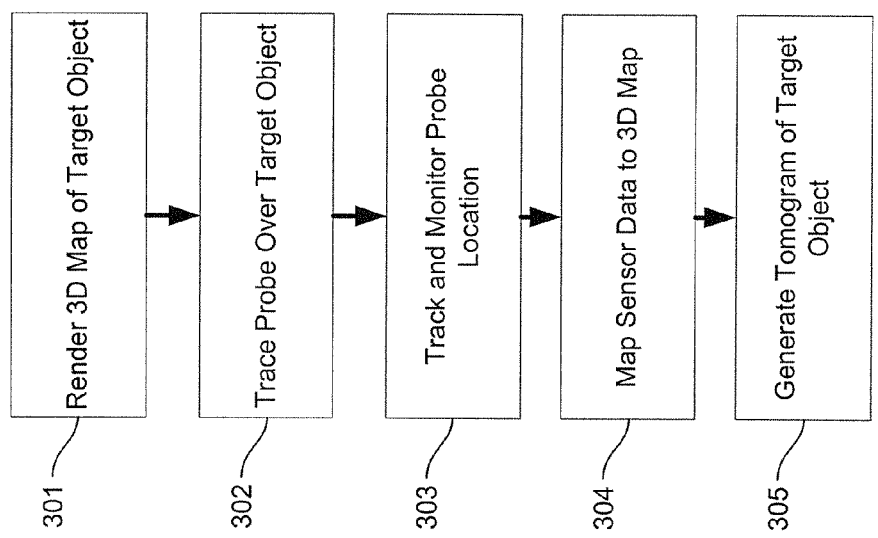
FIG. 19 illustrates a block diagram of a method of producing tomograms of a target tissue object.

FIG. 19 illustrates a process embodiment for producing tomograms of a target tissue object. At block 301, a three-dimensional scanner and appropriate meshing software may be used to render a three-dimensional map 304 (e.g., a mesh of point locations) of the target three-dimensional tissue object. At block 302, a probe may be traced over the target tissue object. As the probe is traced over the target tissue object and sensor data are recorded, the position of the probe may be tracked 303 and recorded using, for example, the tracking system described above. Timed sensor data may then be mapped to a location on the 3-D map 304. In some embodiments, a computer, such as the computer 206 may be programmed to receive sensor data from the probe at a period of time, to receive location information from the tracking system 200 for the period of time, and to map this data to corresponding points on the 3-D map or mesh of the target object. In this manner, a location or coordinate value is associated with the timed sensor data. At block 305 the sensor data may be processed along with the coordinate or location information associated with the sensor data to produce a tomogram of the three-dimensional tissue object using appropriate inverse algorithms.

It should be noted that while some embodiments of the process illustrated in FIG. 19 may be used with an optical imaging probe as described above, the process may be used with other types of probes and sensors to generate a tomographic reconstruction of subsurface structures. For instance, hand-held imaging systems are available in other imaging modalities (e.g. ultrasound, gamma imaging, and electrical impedance tomography), apart from optical imaging. However, to date none of these hand-held imagers (optical or other modalities) are capable of providing 3-D tomography-relevant sensor data. Hence, the process in FIG. 19 can be applied to any hand-held based imaging system listed above. Co-registration of acquired surface data with corresponding location data (as described below), may facilitate implementation of the method of FIG. 19.

In some embodiments, a Bayesian Approximate Extended Kalman Filter (AEKF) based inverse algorithm may be employed for image reconstruction (or tomogram generation) of 3-D optical property maps using location registered sensor data from the 3-D surface of the target object. In brief, the AEKF-based algorithm may employ measurements and system errors to iteratively reconstruct for unknown parameters. The AEKF algorithm may be modified and/or optimized to reflect unique simultaneous illumination and detection measurement geometry of the imager described above, to apply noise filtration techniques to minimize artifacts during inversions; and/or to synchronize the mesh with the real-time co-registered measurements. These modifications may provide computationally efficient reconstructions. Various inverse algorithms have been developed by other researchers, and any one of them may be used instead of AEKF based algorithm.

The embodiments of the optical imaging system and method described above may use multiple simultaneous illuminating point sources with corresponding sequential/simultaneous multiple point detectors to maximize tissue volume illumination and reduce data acquisition times. The measurement geometry may be implemented as a sub-surface imaging geometry, which allows flexible imaging of large tissue volumes with minimal patient discomfort. The optical imaging system and method may have applications not only in breast imaging, but also for any other tissue or phantom imaging.

Moreover, the optical imaging system using tracking facilities and the location/sensor data registration process (FIG. 19) may provide a highly efficient method of reconstructing the optical property maps of 3-D tissue structures including 3-D sub-surface structures. Existing optical tomography towards breast cancer diagnostics is generally restricted to slab geometries representing compressed breast tissues or to cup-shaped breast phantoms of fixed volumes, wherein single point illumination configurations are typically employed. Compression of breast tissue is generally uncomfortable to patients and non-compressive techniques are usually preferred.

Real-Time Co-Registration Software

As described above, co-registration is the process of aligning image data (of a plane or volume) with other image data and/or location data within the same coordinate space. Two types of co-registration techniques exist: intermodality and intramodality. Intermodality co-registration aligns image data of different modalities, whereas intramodality co-registration aligns image data from the same modality. Intermodality co-registration is beneficial because it enables the combination of multiple images (i.e., multiple image types) such that the advantageous characteristics of each are combined into a single image, enhancing the quality of the final image. Intramodality co-registration is beneficial because it enables the alignment of image data at different locations from the same modality such that the data can be used to determine the three-dimensional location of a point of interest or to reconstruct a volume. The disclosed method and system use intramodality co-registration to obtain co-registered, three-dimensional surface images from two-dimensional surface data, which three-dimensional surface images may be used for three-dimensional tomography. Of course, as used herein, the term "real-time" does not necessarily indicate that data and/or images are updated at the same rate or greater rate as the data and/or images are received. As used herein, use of the term "real-time" indicates a lack of significant delay or lag time. For example, the term "real-time" may indicate that an action (e.g., data processing) or event (e.g., display of an image) occurs within as much as several seconds from acquisition of the data, or may indicate that the action or event occurs within a second, or less than a second, from the data acquisition.

Co-registration of probe image data with a discretized 3-D mesh mandates that the geometry of the probed 3-D geometry (with which the image data is being co-registered) be known. The 3-D geometry can be determined by a user's previous knowledge of the 3-D geometry or by using a three-dimensional laser scanner, such as that made by Polhemus Inc, of Colchester, Vt., which automatically acquires the 3-D geometry. Once the tracking system provides the probe location, and the optical image data are obtained using the optical imaging system, the image data can be co-registered onto a discretized 3-D mesh at the true location.

For simple cases in which the 3-D geometry is simple and/or symmetric, a 3-D mesh can be generated within software environments such as MATLAB or GAMBIT (Fluent Inc., Lebanon, N.H.). However, for complex geometries it would be too time consuming to manually measure a 3-D geometry and generate a corresponding 3-D mesh. Thus, for complex geometries, a Polhemus-brand (Colchester, Vt.) three-dimensional laser scanner, or other similar system, may be used to acquire three-dimensional surface geometries of real-world objects by scanning them with the hand-held laser scanner. To do so, the scanner is passed multiple times over the 3-D geometry to be imaged until the scanner acquires enough data to reconstruct the surface geometry. The reconstructed surface geometry can then be meshed and uploaded into the co-registration software where the optical image data is co-registered with the 3-D mesh as described below.

Figure 20A:
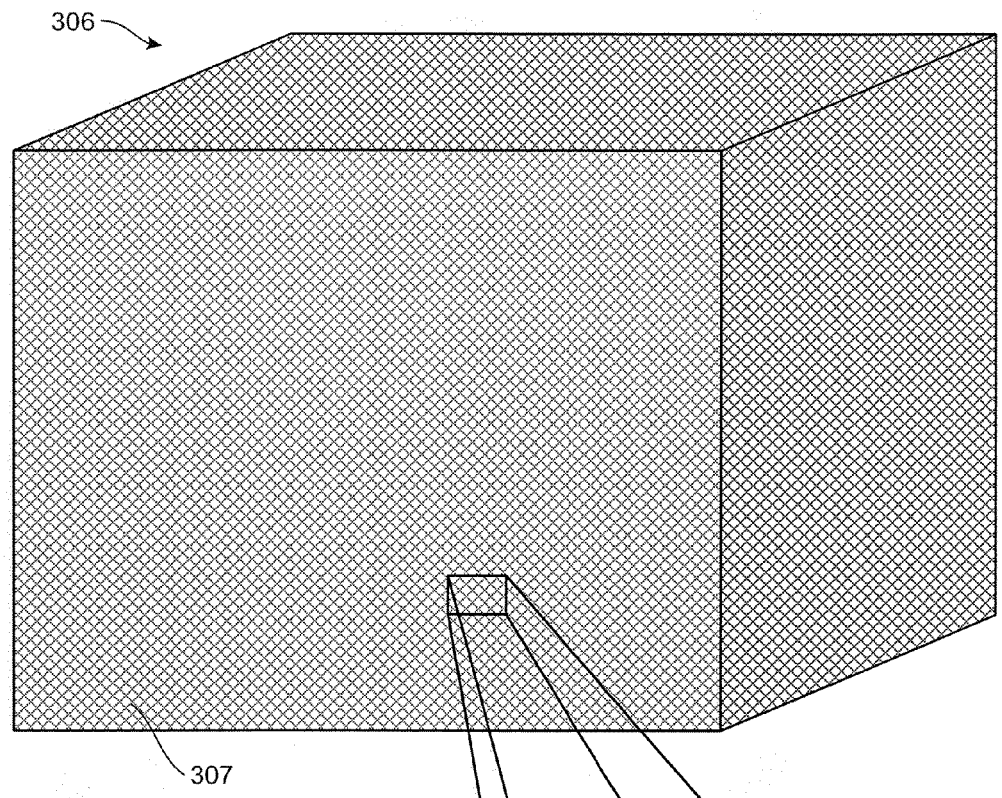
FIG. 20A depicts an exemplary 3-D mesh in accordance with the presently described system.
Figure 20B:
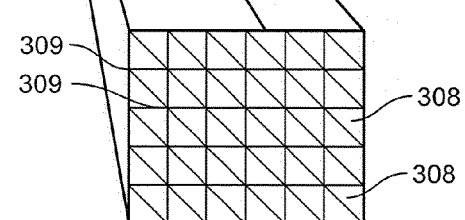
FIG. 20B depicts an enlarged view of a portion of the exemplary 3-D mesh of FIG. 20A.
Figure 20C:
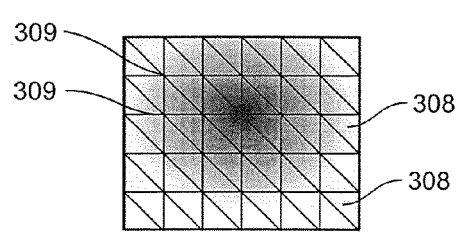
FIG. 20C depicts the enlarged view of FIG. 20B after co-registration of data has been performed.

FIGS. 20A and 20B depict, respectively, a 3-D mesh 306 having a surface 307, and an enlarged portion of the 3-D mesh 306, showing the surface 307 discretized into a plurality of triangular faces 308 and vertices 309. To co-register optical image data with the 3-D mesh 306, each data point (i.e., data from each of the detectors on the probe) is co-registered with a vertex 309 that is nearest to the detection point on the 3-D mesh's surface 307, and the corresponding face 308 is assigned an appropriate optical intensity-equivalent color value based on the data. Prior to co-registration of current data with the 3-D mesh 306, the color on the surface 307 of the 3-D mesh 306 will be dependent on whether or not previous image data have been co-registered onto the 3-D mesh 306. FIG. 20C depicts an enlarged view of FIG. 20B after co-registration.

Figure 21A:
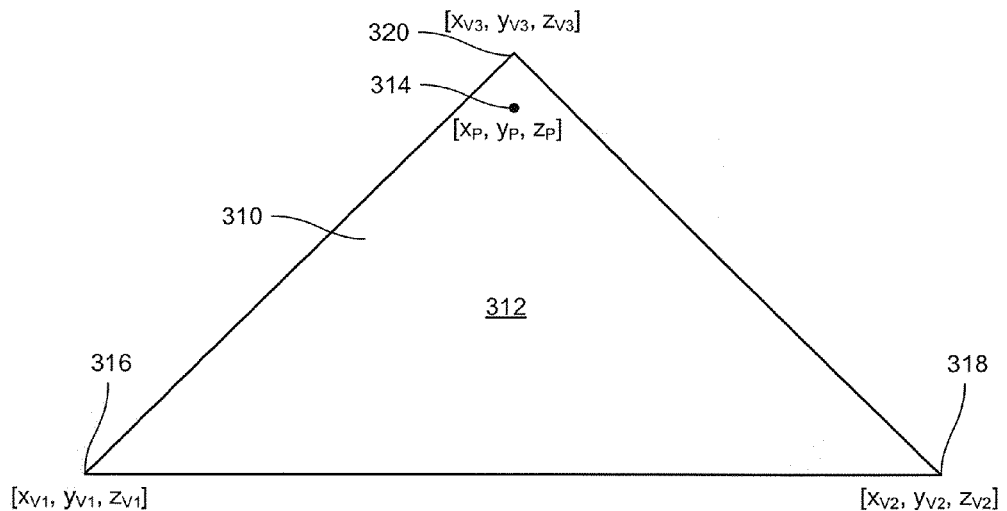
FIG. 21A illustrates a single fiber optic point placed randomly on a triangular face of the 3-D mesh surface illustrated in FIG. 20B.

With reference to FIG. 21A, when a single triangular face 308, such as the triangular face 310, defines a surface 312 of a 3-D mesh (such as the 3-D mesh 306), the triangular face 310 is defined by three vertices 316, 318, 320, at points $[x_V, y_V, z_V] = [x_{V1}, y_{V1}, z_{V1}; x_{V2}, y_{V2}, z_{V2}; x_{V3}, y_{V3}, z_{V3}]$, respectively. A single fiber optic point 314 is placed randomly on the surface 312 of the triangular face 310 at a point $[x_P, y_P, z_P]$. By determining the distance $V_D$ from each vertex 316, 318, 320, the closest vertex to the point 314 can be calculated by finding the minimum value from a set of $V_D$ values.

The algorithm (described below) implemented to calculate optical intensity-equivalent color values detected at each point of the 3-D mesh 306 may be a vertex-by-vertex implementation in which a distance $V_D$ of a fiber optic point from every vertex 309 on the 3-D mesh 306 is calculated by a computer (not shown). $V_D$ may be determined according to the equation:

$$V_D = \sqrt{dx^2 + dy^2 + dz^2} = \sqrt{(x_V - x_P)^2 + (y_V - y_P)^2 + (z_V - z_P)^2} \quad \text{(Equ. 1)}$$

The minimum distance from the set of values may be determined by the computer and the point correlating with that minimum distance is assigned the optical intensity-equivalent value of the point on the probe. The colors of the triangular faces 308 are determined by interpolation of each vertex 309 of the triangular faces 308 via the software.

Figure 21B:
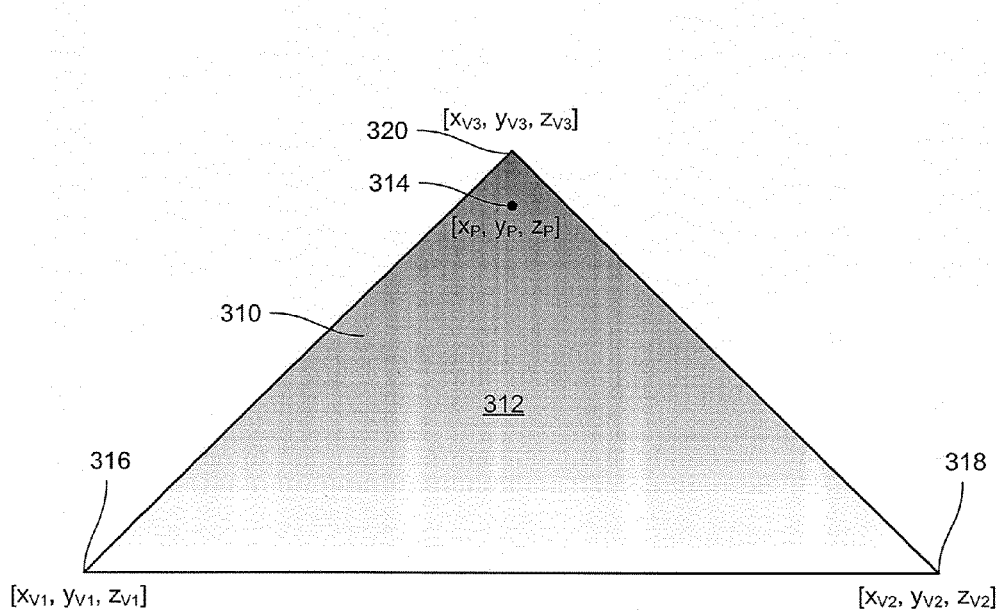
FIG. 21B illustrates the coloring of the triangular face of FIG. 21A after execution of a coloring algorithm.

Once a minimum for $V_D$ is found by the computer, the optical intensity-equivalent color value at the single fiber optic point 314 can be assigned to the nearest vertex (e.g., the vertex 320) and the values of all other vertices 316, 318 can be interpolated to enable shading of the triangular face 310. In FIG. 21B, the fiber optic point 314 is near the top vertex 320 of the triangular face 310. Accordingly, the vertex 320 is assigned a color, corresponding to an optical intensity of at the fiber optic point 314.

For 3-D meshes with a small number of vertices, the aforementioned algorithm is sufficient. However, as the complexity of the geometry of a 3-D mesh increases, the number of vertices 309 and faces 308 must be increased to better resolve intricate patterns of curvature in the geometry. This amounts to a 3-D mesh with many more vertices and faces than a simple case. The aforementioned algorithm implements a vertex-by-vertex search over the entire 3-D mesh, making it computationally inefficient in cases where high mesh resolution is required.

To address this problem, exclusion code logic is implemented whereby only 3-D mesh vertices 309 within a certain range 'b' (buffer zone) of the probe face are incorporated into minimum distance calculations. This buffer zone can range from b=0, where only the 3-D mesh vertices in direct contact with the probe are searched, to b=the maximum length of 3-D mesh, in which case all vertices of the 3-D mesh are included in the search. This significantly decreases processing time for large 3-D meshes depending, of course, on the processing hardware on which the software embodiment of the algorithm is running.

As much as the processing hardware may affect the processing time for large 3-D meshes, achieving automated real-time co-registered imaging requires minimal time delay between data acquisition and display. A major concern during automated real-time co-registration is that several processes need to be running simultaneously, some of which may demand considerable processing time and thereby increase the time lag between the acquired and displayed time. These processes are (in descending order of computational demand): (i) co-registration of image data onto the correct location of 3-D mesh; (ii) real-time image data acquisition; (iii) the saving/display of data; (iv) real-time tracked location of probe; and (v) miscellaneous background processes (e.g., antivirus, web browser, etc.). The simplest solution resulting in decreased time lag and, thereby, increased processing speed, is to implement one or all of the following: (i) close all unnecessary background processes; (ii) increase random access memory (RAM); and (iii) increase processing capabilities (i.e., faster central processing unit (CPU) and increased RAM). In the disclosed embodiment, the issue is addressed by using a state of the art workstation computer dedicated strictly to this system.

Implementing efficient programming code is also important in a well-built co-registration program. Moreover, an intuitive graphic user interface (GUI) facilitates the process by providing users with a dynamic array of options meant to enhance visualization and display schemes as well as optimize data processing techniques. Some of the features of the developed co-registration software are its powerful ability to: (i) upload any set of face and vertex data corresponding to a 3-D mesh; (ii) adjust the on-screen position/orientation of a 3-D mesh to match its real-time location; (iii) use simulated or real-time image data in co-registration; (iv) auto-normalize color data over the range of intensities of an entire co-registered 3-D mesh; (v) retain/erase image data acquired during a previous scan; (vi) acquire and display real-time probe location/orientation; (vii) adjust the on-screen angle of the probe's outer plates to match its real-time angles; and (viii) save all displayed information into a single file (e.g., a MATLAB .mat file) for post-process analysis.

Figure 22:
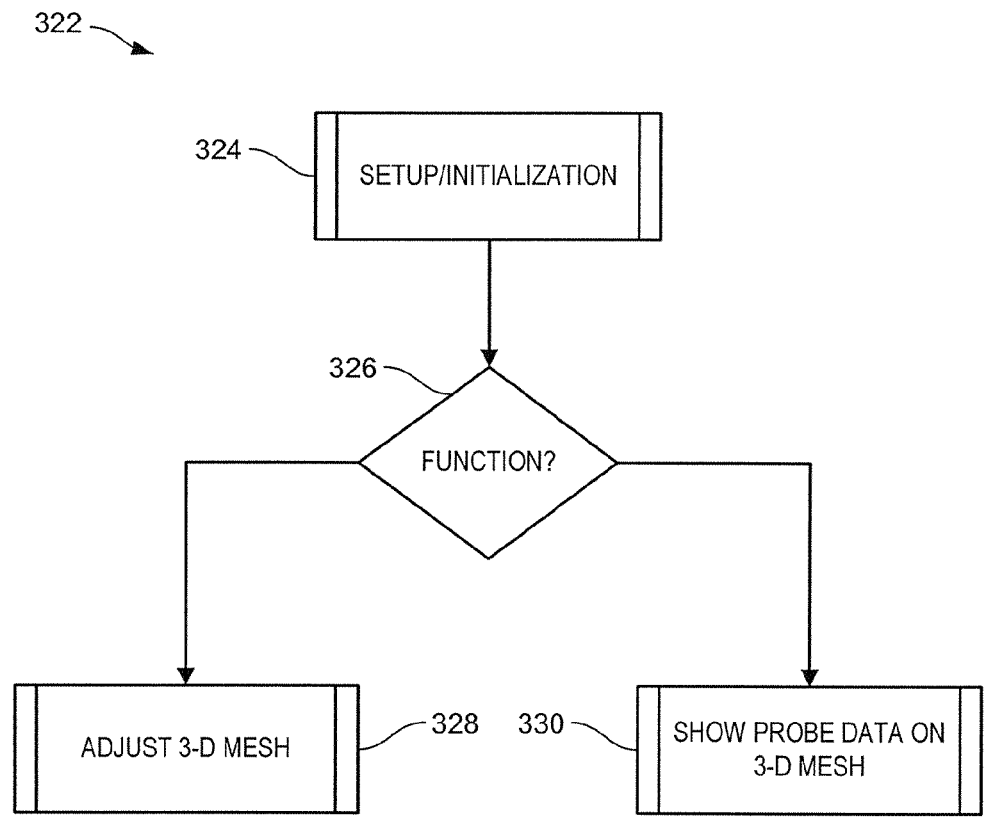
FIG. 22 depicts a method for performing co-registration in accordance with the presently described system.

Real-time co-registration software processes and displays the image data received from the probe, using the data of the 3-D mesh and the data of the probe location. The software may be implemented in any suitable high-level programming language such as, for example, MATLAB, LabVIEW, C, C++, etc., or in a combination of high-level programming. In some embodiments, the software is implemented in a combination of MATLAB and LabVIEW. In particular, a disclosed embodiment implements MATLAB code included in a program written in the LabVIEW programming language to automate the process of image data and probe location data acquisition such that as the tracker changes the location coordinates and orientation, the software updates the location and orientation of the probe—and thus the location of the corresponding image data—accordingly, with minimal lag in real-time. The software implements a method, similar to a method 322 in FIG. 22, the software including one or more routines and/or sub-routines. The method 322 begins with setup/initialization (block 324). The software may determine (block 326) what the user wants to display in accordance with an input from a graphical user interface (GUI). The software may then run a routine to adjust the 3-D mesh (block 328) or a routine to show the probe data on the 3-D mesh (block 330).

Prior to initiating the method 322, the software may display the GUI to collect information from the user, including parameters such as a file name, the parameters (e.g., vertices and faces) of the 3-D mesh (or directories where files containing the parameters are stored), a COM port number from which to read the probe data and/or the location of the probe 80, calibration values for CCD hardware on the probe, a receiver center location with respect to the probe, a relative position of the 3-D mesh, viewing angles, probe reference location, 3-D mesh resolution, etc. The user may place the hand-held probe 80 on a fixed reference point. Upon execution of the method 322, the software setup/initialization (block 324) reads the parameters defined by the user and initializes the probe location as the origin of the coordinate space (i.e., [x, y, z]=[0, 0, 0] cm).

Figure 23:
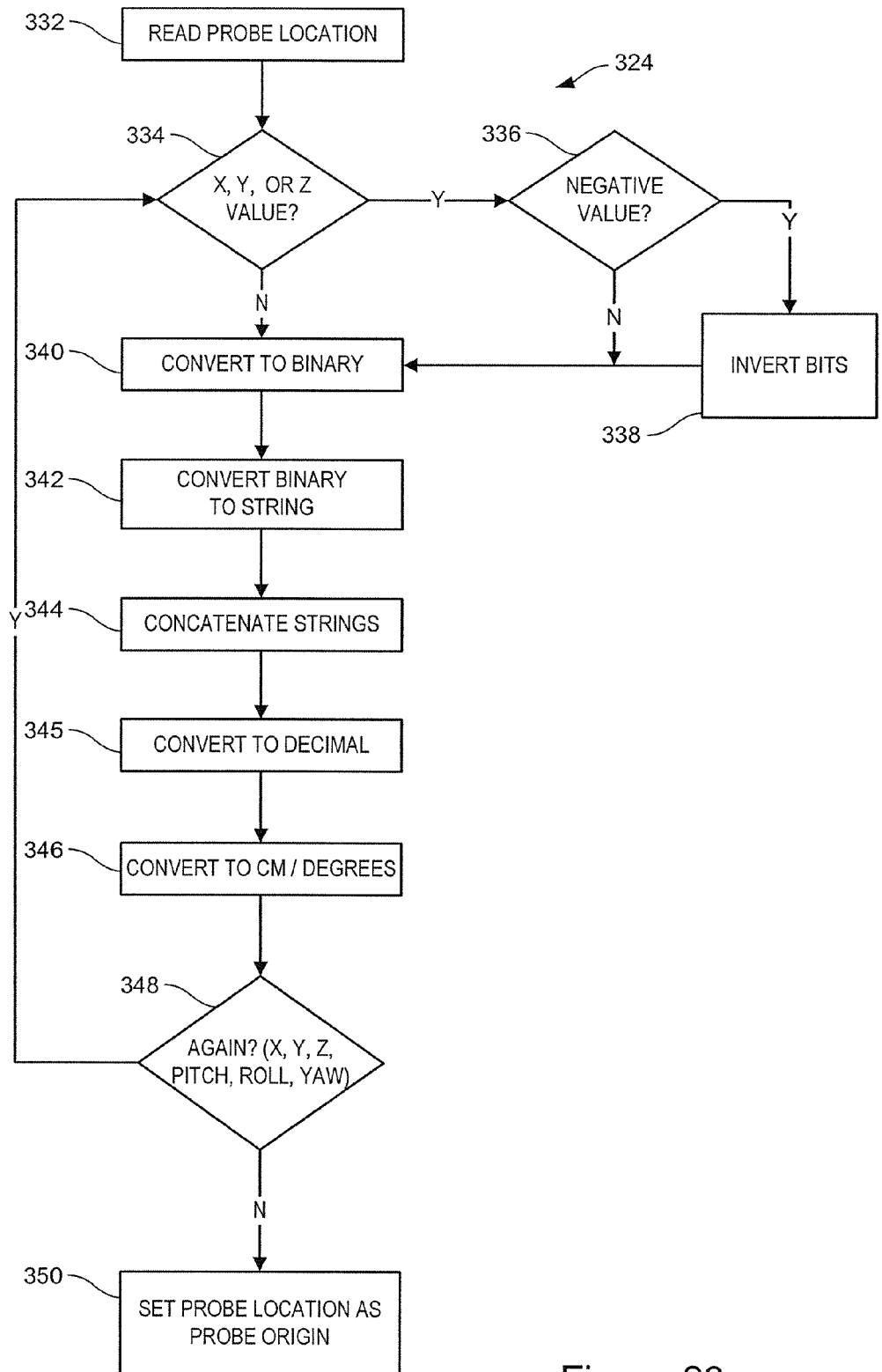
FIG. 23 depicts an embodiment of a method for setting up and initializing the presently described system.

Initialization of the probe location, illustrated in FIG. 23, begins by reading the probe location (block 332). The probe location is determined by a tracker device (e.g. the tracker system 200). Some embodiments of the co-registration system disclosed utilizes an acoustic based tracker, such as that manufactured by Logitech Inc., of Fremont, Calif., that is suitable for use with a hand-held probe based optical imaging system. The acoustic tracker employed operates in the ultrasonic range, which mitigates or eliminates any interference issues between the optical imaging system and the acoustic based tracker. Many acoustic tracking systems, such as that utilized in the disclosed embodiment of the system, allow the tracking system to determine the location of a tracked object with six degrees of freedom. That is, the system determines the object's position (in x, y, and z coordinates) as well as the object's orientation in space (in pitch, yaw, and roll). Other embodiments may use other tracking systems, such as an optical tracking system. However, many optical tracking systems operate in the same electromagnetic spectral range as the optical imaging system (near-infrared light). Thus, when designing the system any embodiment using an optical tracking system will require special consideration of issues relating to optical interference.

The computer running the co-registration software may read the probe location directly from the tracker via a data connection to the tracker (e.g., a direct connection via an RS-232 port). In some embodiments, the data received from the tracker are in the form of a 16×1 vector of binary data in Sixteen-Byte format, as depicted in FIG. 24. The data provided by the tracker include a bit ("FRI") indicating that the tracker has entered fringe space (i.e., a space near the edge of the detection space); a bit ("OUT") indicating that the tracker is out of range (i.e., that the tracker has moved out of the detection space); five bits ("P", "S", "L", "M", and "R") that are used in conjunction with mouse tracking applications and are not used in the disclosed system; twenty-one bits, X20 to X0 (Byte 2 to Byte 4), that indicate distance in a direction X; twenty-one bits, Y20 to Y0 (Byte 5 to Byte 7), that indicate distance in a direction Y; twenty-one bits, Z20 to Z0 (Byte 8 to Byte 10), that indicate distance in a direction Z; fourteen bits, PI13 to PI0 (Byte 11 to Byte 12), that indicate pitch rotation; fourteen bits, YA13 to YA0 (Byte 13 to Byte 14), that indicate yaw rotation; and fourteen bits, RO13 to RO0 (Byte 15 to Byte 16), that indicate roll rotation. Of course, other tracking systems may have higher resolution (i.e., have more bits of data) for any of the various parameters, or lower resolution (i.e., have fewer bits of data) for any of the various parameters. Moreover, some systems may have greater or lesser tracking range, may use the mouse tracking bits for some purpose (e.g., reporting various conditions of the tracking system), or may have bits that provide other information (e.g, battery strength if the device is battery-operated, signal strength if the system is wireless, image capture indicators, or any other type of signal as desired).

After reading the probe location and/or orientation data (block 332), the software may perform a series of conversion steps (blocks 334-346) to convert the probe location and/or orientation data into a proper and/or usable format. For example, in one disclosed embodiment, the probe location data read from the tracker have a resolution such that each bit in the X, Y, and Z fields represents a space of $\frac{1}{1000}$ inch (i.e., the tracker has a $\frac{1}{1000}$ inch resolution), and the probe orientation data (i.e., pitch, roll, yaw) have a resolution of $\frac{1}{40}$ degree. The series of conversion steps (blocks 334-346) may convert the probe location data (e.g., X, Y, and Z coordinates), for example, into centimeters, and may convert the probe orientation data (e.g., pitch, roll, and yaw) into degrees. For each location coordinate X, Y, and Z (block 334) the software may determine (block 336) whether the value indicated is positive or negative. If the value is negative, the software may invert the bits (block 336) before proceeding with the remainder of the conversion. Each byte of probe location data (e.g., bytes 2 through 4 for the X coordinate) is converted to a binary value (block 340), which is converted to a string (block 342). The three string values (one for each byte of the coordinate) are concatenated (block 344) and the resulting string value is converted back from binary to decimal form (block 345 and multiplied by a conversion factor (e.g., 0.00254 to convert $\frac{1}{1000}$ inch into centimeters) (block 346). If there are additional data to convert (e.g., the Y and Z coordinates), the conversion (blocks 334-346) is repeated (block 348).

Similarly, the software may convert (at blocks 340-346) the probe orientation data (e.g., bytes 11 through 12 for pitch) to a binary value (block 340), which is converted to a string (block 342). The two string values (one for each byte of the pitch, the roll, or the yaw) are concatenated (block 344) and the resulting string value is converted back from binary to decimal form (block 345) and multiplied by a conversion factor (e.g., 0.025 to convert to degrees) (block 346). If there are additional data to convert (e.g., roll and yaw), the conversion (blocks 334-346) is repeated (block 348). Having determined the location coordinates and the orientation of the probe 80 (while the probe 80 is at a fixed reference point), the software sets the probe location as the probe origin (block 350).

Figure 25:
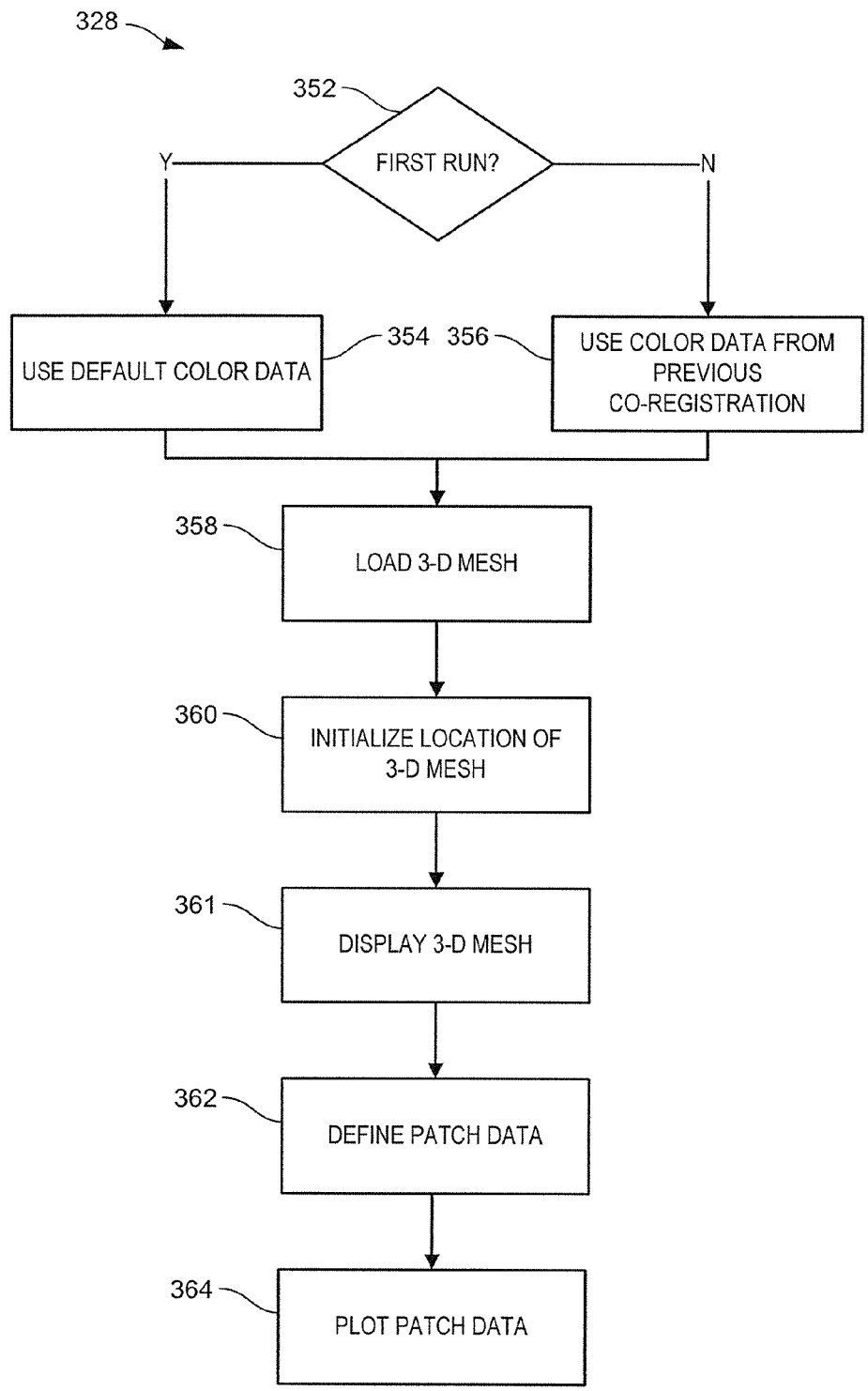
FIG. 25 depicts a method of adjusting a 3-D mesh in accordance with an embodiment of the presently described system.

If the software determines (at block 326) that the user has indicated through the GUI to show the 3-D mesh and allow adjustments (block 328), the software may proceed as illustrated in FIG. 25 (blocks 342-364). If the software is executing the block 328 for the first time since the software was executed (i.e., no co-registration has yet been performed) (determined at block 352), the software may use the default color data for the vertices and faces of the 3-D mesh (block 354). Alternatively, if the software is not executing the block 328 for the first time since the software was executed (i.e., if the option is selected so that the user may adjust the position of the 3-D mesh), the software may use color data from previous co-registration (block 356).

In any event, in a disclosed embodiment the software loads the 3-D mesh (block 358), for example from the files specified in the GUI by the user. The location of the 3-D mesh is locked to the origin (block 360) determined previously (at block 350). The 3-D mesh may be displayed at this point (block 361). In some embodiments, the software creates a visual display of the 3-D mesh that depicts the entire 3-D mesh as having a single color because no color data have yet been overlaid on the 3-D mesh. In some embodiments, the software will depict the 3-D mesh as having the colors associated with the data from the previous measurements. The software may then define, by patch data, a patch (i.e., may specify the coordinates that define the vertices of each face and the elements that define the connectivity of each face) (block 362) of a probe mesh corresponding to the probe face and with which probe color data may be aligned.

The software next may plot the patch data (block 364) as a three-dimensional probe mesh with respect to the 3-D mesh. The points on the probe mesh correspond to the ends of the detector fibers. The location of each detector fiber is specified by a set of x, y, and z coordinates. Of course, when the probe faces 61-63 are not angled with respect to each other, the location of each detector fiber will be in the same plane and, therefore, could be specified by two coordinates. In some embodiments, plotting the patch data includes getting the vertices data, adding values of dx, dy, and dz (which may be received via the GUI) to the data so that the 3-D mesh and the probe mesh can be moved in real time according to inputs via the GUI from the user, and/or getting the pitch, yaw, and roll data. In some embodiments, getting the pitch, yaw, and roll data may include defining an x-axis of the 3-D mesh, defining a y-axis of the 3-D mesh, defining a z-axis of the 3-D mesh, and/or defining a center of the 3-D mesh. In at least one embodiment, the 3-D mesh may be symmetrical about the defined x- and y-axes so that the software may rotate the 3-D mesh around the center point of the 3-D mesh. In some embodiments, the z-axis remains fixed so that the 3-D mesh remains constant on the z-plane.

Figure 26:
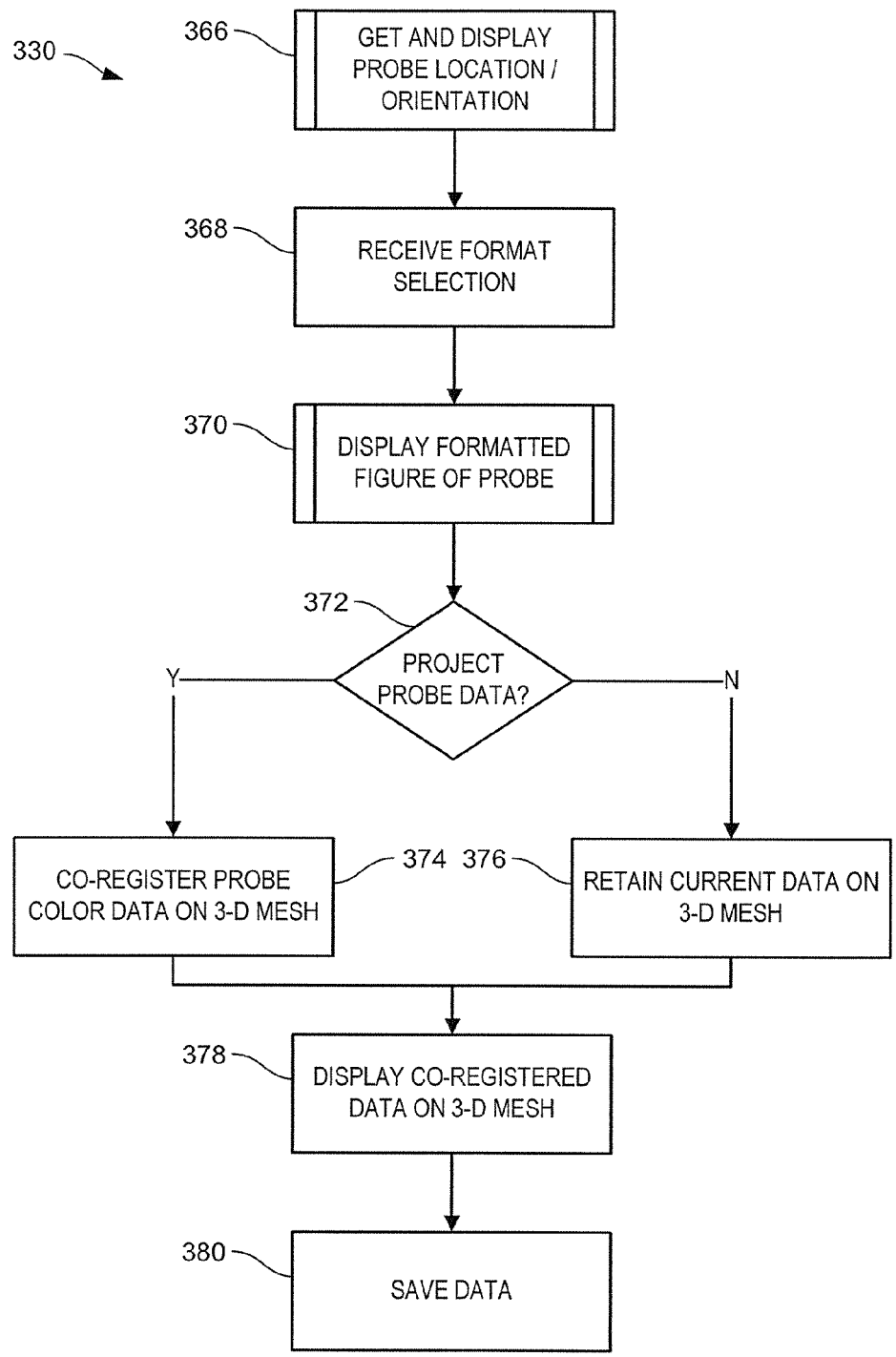
FIG. 26 depicts a method of displaying probe data on a 3-D mesh in accordance with an embodiment of the presently described system.
Figure 27:
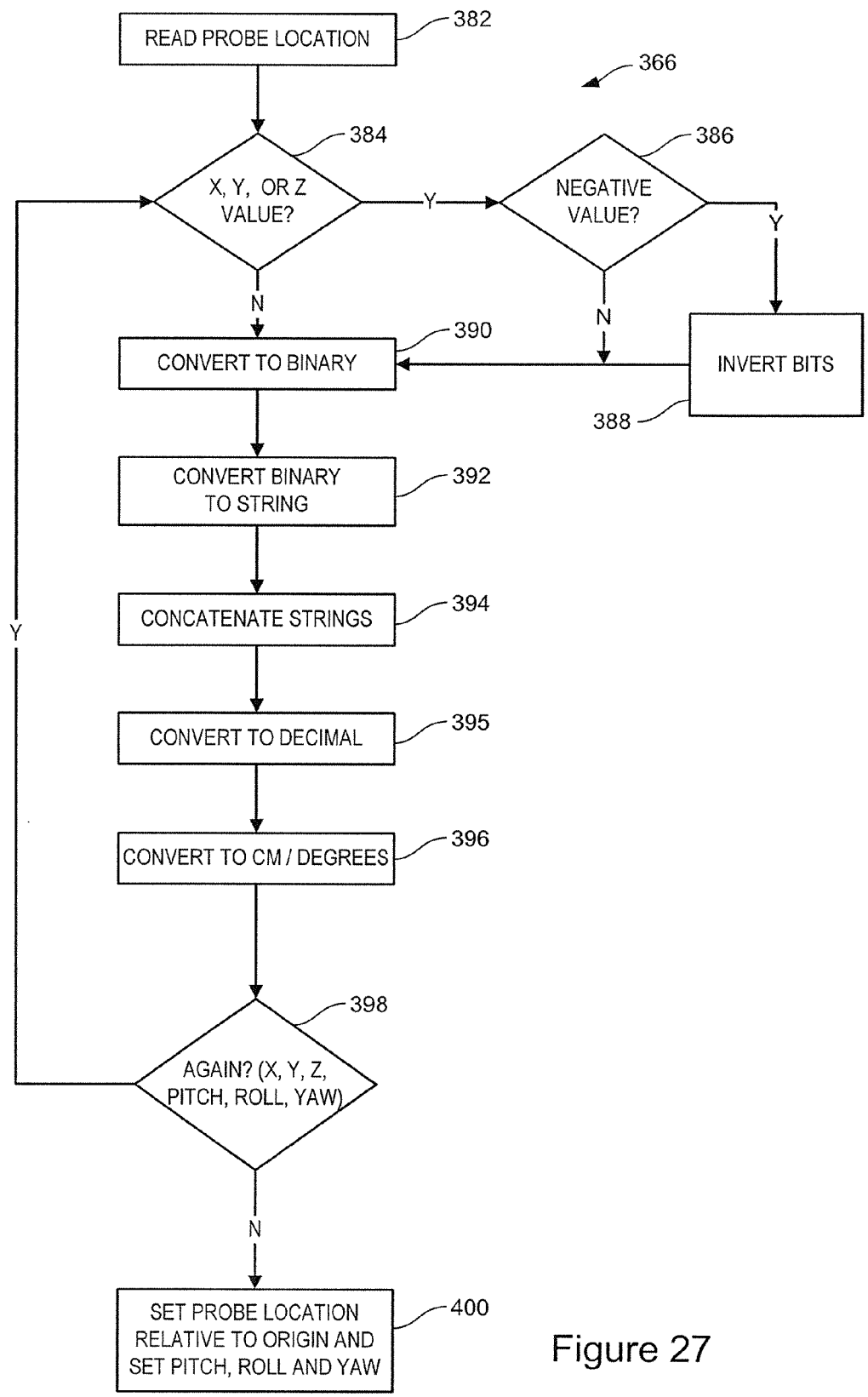
FIG. 27 depicts a method of displaying probe location and orientation in accordance with an embodiment of the presently described system.

If instead the software determines (at block 326) that the user has indicated through the GUI to show the probe relative to the 3-D mesh (block 330), the software may proceed as illustrated in FIG. 26 (blocks 366-380). The software may first determine and display the position and orientation of the probe 80 (block 366). With reference now to FIG. 26, determining the probe location and orientation (block 366) proceeds similarly as during initiation (block 324). That is, for the embodiment described above with reference to FIG. 23, the software may read the probe location (block 382), and the software may perform a series of conversion steps (blocks 384-396) to convert probe location and/or orientation data into a proper format. The series of conversion steps (blocks 384-396) may convert the location data (e.g., X, Y, and Z coordinates), for example, into centimeters, and may convert the orientation data (e.g., pitch, roll, and yaw) into degrees. For each location coordinate X, Y, and Z (block 384) the software may determine (block 386) whether the value indicated is positive or negative. If the value is negative, the software may invert the bits (block 388) before proceeding with the remainder of the conversion. Each byte of data (e.g., bytes 2 through 4 for the X coordinate) is converted to a binary value (block 390), which is converted to a string (block 392). The three string values (one for each byte of the coordinate) are concatenated (block 394) and the resulting string value is converted back from binary to decimal form (block 395) and multiplied by a conversion factor (e.g., 0.00254 to convert 1/1000 inch into centimeters) (block 396). If there are additional data to convert (e.g., the Y and Z coordinates), the conversion (blocks 384-396) is repeated (block 398).

Similarly, the software may convert (at blocks 390-396) the orientation data (e.g., bytes 11 through 12 for pitch) to a binary value (block 390), which is converted to a string (block 392). The two string values (one for each byte of the pitch, the roll, or the yaw) are concatenated (block 394) and the resulting string value is converted back from binary to decimal form (block 395) and multiplied by a conversion factor (e.g., 0.025 to convert to degrees) (block 396). If there are additional data to convert (e.g., roll and yaw), the conversion (blocks 384-396) is repeated (block 398). Having determined the location coordinates and the orientation of the probe 80, the software sets the probe location relative to the origin (determined at the block 350) (block 400).

Figure 28:
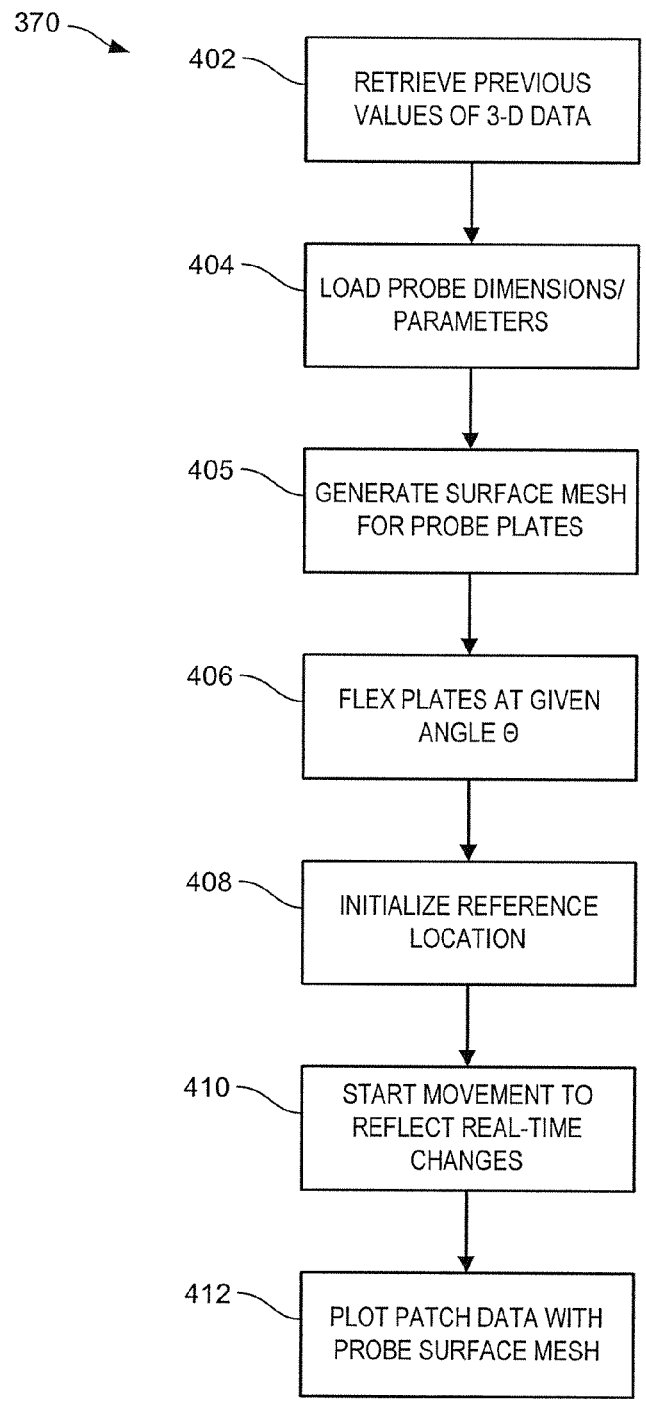
FIG. 28 depicts a method of displaying a formatted figure of a probe in accordance with an embodiment of the presently described system.

With reference again to FIG. 26, the software may determine one or more parameters related to the probe and/or the 3-D mesh format received from the user through the GUI (block 368). When the one or more parameters have been received, the software displays the formatted figure of the 3-D mesh with the probe (block 370). With reference now to FIG. 28, displaying the formatted figure of the 3-D mesh with the probe may include retrieving previous values of 3-D mesh data (block 402). The 3-D mesh data may be used at a later point when the user selects to adjust the 3-D mesh. The software may also load information about probe dimensions and/or parameters (block 404), including information about probe width, information about probe height, real-time image color data, resolution factor of the 3-D mesh, point locations along the width of the probe of the hinges where the plates of the probe flex, angles theta ($\theta$) of the side plates with respect to the center plate, etc. The software next generates a 3-D probe mesh for the probe plates (block 405). That is, the software will determine the position of each of the detector fiber ends on the probe plates, and generate a corresponding 3-D probe mesh, according to the information and/or parameters determined (block 404). Once the 3-D probe mesh for the probe face has been generated (block 405), the software adjusts the position of the detector fiber ends according to the given angle theta ($\theta$) (block 406) as determined from the information specified by the user through the GUI (block 404).

Following the generation of the 3-D probe mesh corresponding to the probe plates with the appropriate plate angles, the software may initialize reference location (block 408). This may include one or more of setting the location of the tracker with respect to the probe face origin, retrieving the initial positional data (x, y, and z locations) for each of the points on the probe (obtained during setup (block 324)), setting the new positional data for each point on the probe by adding the current data to the initial data, and saving the new positional data for each of the points on the probe faces. It may also include defining the x, y, and z axes of the probe, defining the rotation of the probe about each of the x, y, and z axes (i.e., the pitch, yaw, and roll values for the probe), and rotating the probe image about each of the axes according to the rotation of the probe. The surface mesh corresponding to the probe surface may be updated in real time.

After initializing the reference location (block 408), the software may begin real-time tracking and movement of the probe location (block 410). The real-time tracking and movement of the probe location may include updating the surface mesh for the probe (i.e., the probe mesh) to reflect changes to the location and orientation of the probe. Lastly, the software may process the color data of the patch currently imaged by the probe, and combine the patch color data with the probe surface mesh (block 412). This results in a real-time image of the surface imaged by the probe.

Referring again to FIG. 26, the software may next determine (block 372) whether the user has, through the GUI, indicated a desire to project the image of the current probe data (color data) onto the 3-D mesh of the object being probed. If the software determines that the user has selected for the projection of the color data onto the 3-D mesh, the software may co-register current probe color data on the 3-D mesh (block 374) (i.e., may co-register the probe mesh with the 3-D mesh). This may require rounding of location data, or other similar mechanisms, to allow the software to superimpose the color data for the probe patch onto the 3-D mesh vertices. For example, if a 3-D mesh vertex location is 23.124 and a probe patch vertex location is 23.125, then the values for the "two" vertices are obviously the indicative of the same vertex. The software may allow for rounding the numbers so each reflects a value 23.12 and allows the software can reassign the color data accordingly. Alternatively, if the software determines that the user has not selected for the projection of the data onto the 3-D mesh, the software may co-register default or previous probe color data on the 3-D mesh (block 376). The software then displays the co-registered data on the 3-D mesh (block 378). Optionally, the software may save the data (block 380).

Of course, it will be apparent that the imaging data (i.e., color data) obtained at each of the detector point locations on the probe may be co-registered with the 3-D mesh of the object being imaged, instead of first co-registering the imaging data from each detector point location with a 3-D mesh of the probe (i.e., the probe mesh) and then co-registering the probe mesh along with the imaging data on to the 3-D mesh. Thus, in some embodiments, the probe color data may be projected directly onto the 3-D mesh of the imaged object, while in some other embodiments the probe color data may be projected onto a probe mesh representative of the probe face, which may, in turn, be co-registered (i.e., aligned) with the 3-D mesh of the imaged object. Additionally, in a disclosed embodiment the probe may be displayed (with or without the probe mesh) in some embodiments, the probe may not be displayed at all, or the probe mesh may be displayed without the probe.

Figure 29:
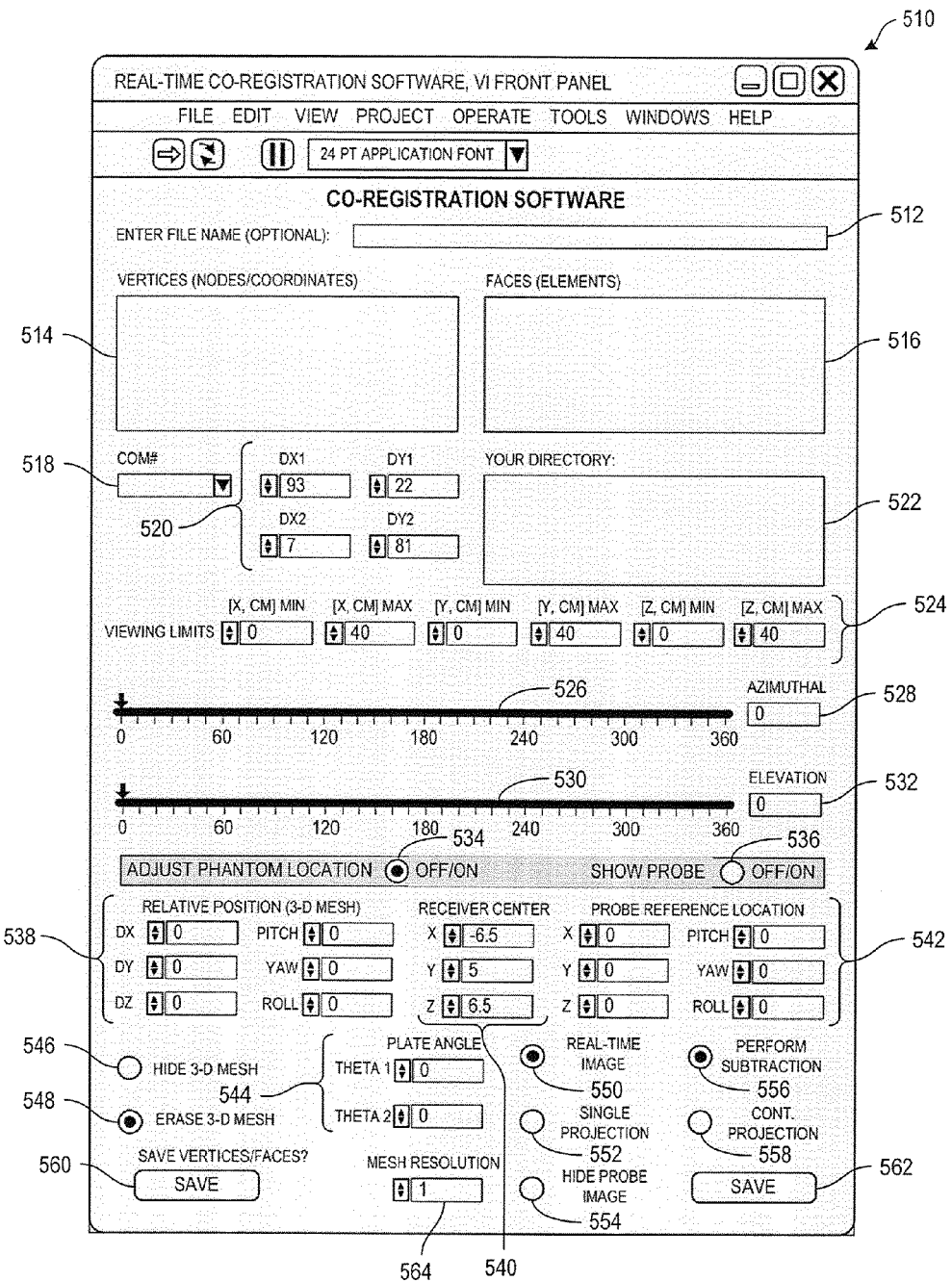
FIG. 29 depicts a graphical user interface (GUI) for use with an embodiment of software in accordance with the presently described system.

FIG. 29 depicts an exemplary graphical user interface 510 that may cooperate with the software embodying the methods described above with reference to FIGS. 23 and 25-28. The GUI 510 may include a file name entry field 512, for allowing the user to choose a file name. Alternatively, if the user does not enter a file name into the file name entry field 512, the program may automatically create a file name in a default format (e.g., a naming convention including date and time). The GUI also includes fields 514, 516 for entering folder directory information in which data defining the vertices and the faces of the 3-D mesh may be located. Another directory entry field 522 may allow a user to enter a directory containing all of the data pertinent to a single run of the co-registration software.

A data entry field 518, which may be a text field, a pull-down menu, etc., may allow a user to specify the serial port (COM port) of the host computer to which the tracking system 200 is connected. The GUI 510 may further include a plurality of data entry fields 520 that may allow a user to input calibration values for the CCD camera connection.

Similarly, a plurality of data entry fields 524 may allow the user to input viewing limits to indicate the 3-D boundary within which a region of interest is viewed. The user may also specify the angle from which region of interest specified in the fields 524 is viewed during operation of the co-registration software. For example, the user may enter an azimuthal angle into a text field 528, or may adjust the azimuthal angle by adjusting a slider bar 526 (the value of which may be reflected in the text field 528). Similarly, the user may enter an elevation angle into a text field 532, or may adjust the elevation angle by adjusting a slider bar 530 (the value of which may be reflected in the text field 532).

A button 534 may allow a user to adjust the on-screen 3-D mesh location to match the true physical location of the depicted object within the coordinate plane. Using a collection of data entry fields 538 to adjust the relative position of the 3-D mesh, the user may display the 3-D mesh in any desired position (dx, dy, dz) and orientation (pitch, yaw, roll) in a virtual coordinate plane (representative of the physical plane in which the object lies). Additionally, using a data entry field (not shown), the user may adjust the on-screen size of the 3-D mesh by a factor defined by field. This may be particularly useful for unit conversions. By activating a button 560, the user may save the current on-screen position of the 3-D mesh for later use. A button 536 may allow a user to display the location of the probe 80 once the object location has been specified using the controls 534 and 538.

By activating a button 546, the user may cause the software to hide the 3-D mesh from view. Similarly, by activating a button 548, the user may erase any surface contour plots present from previous co-registrations. Otherwise the co-registered images may be retained and used as a reference for other co-registrations.

A plurality of data entry fields 540 allow the user to specify, with respect to the probe 80, the center of the receiver used to track the probe 80.

A plurality of data entry fields 542 allow the user to specify a physical location and orientation of the probe with respect to the coordinate plane when the probe is placed on a reference location. A plurality of controls 544 allow the user to specify the angles of probe faces with respect to one another.

A data entry field 564 may allow the user to adjust the resolution (mesh size) to the user's preference.

A plurality of buttons 550-558 allow the user to specify how the software should perform and how the software should display any images. For example, a button 550 may cause the software to represent default simulated image color data or the real-time fluorescence intensity image color data detected by the probe 80. A button 552 may cause the software to project current probe color data onto the 3-D mesh (i.e., only current data, data later acquired) where it is no longer displayed separate from the 3-D mesh but as an inherent component, while a button 558 may cause the software to project the probe color data onto the 3-D mesh continuously even as the probe 80 is moving. A button 556 may cause the software to subtract the background image color data from the real-time image color data (i.e., to display a differential image of current color data and color data of the object absent a target). This may be useful in calibrating and/or testing the device on a phantom object, or in detecting changes in the tissue object over time. A button 554 may cause the software to hide the on-screen image of the probe 80 to allow the user to better view the 3-D mesh.

A button 562 may allow the user to save into a file any on-screen data displayed at the time the user activates the button 562.

Figure 30:
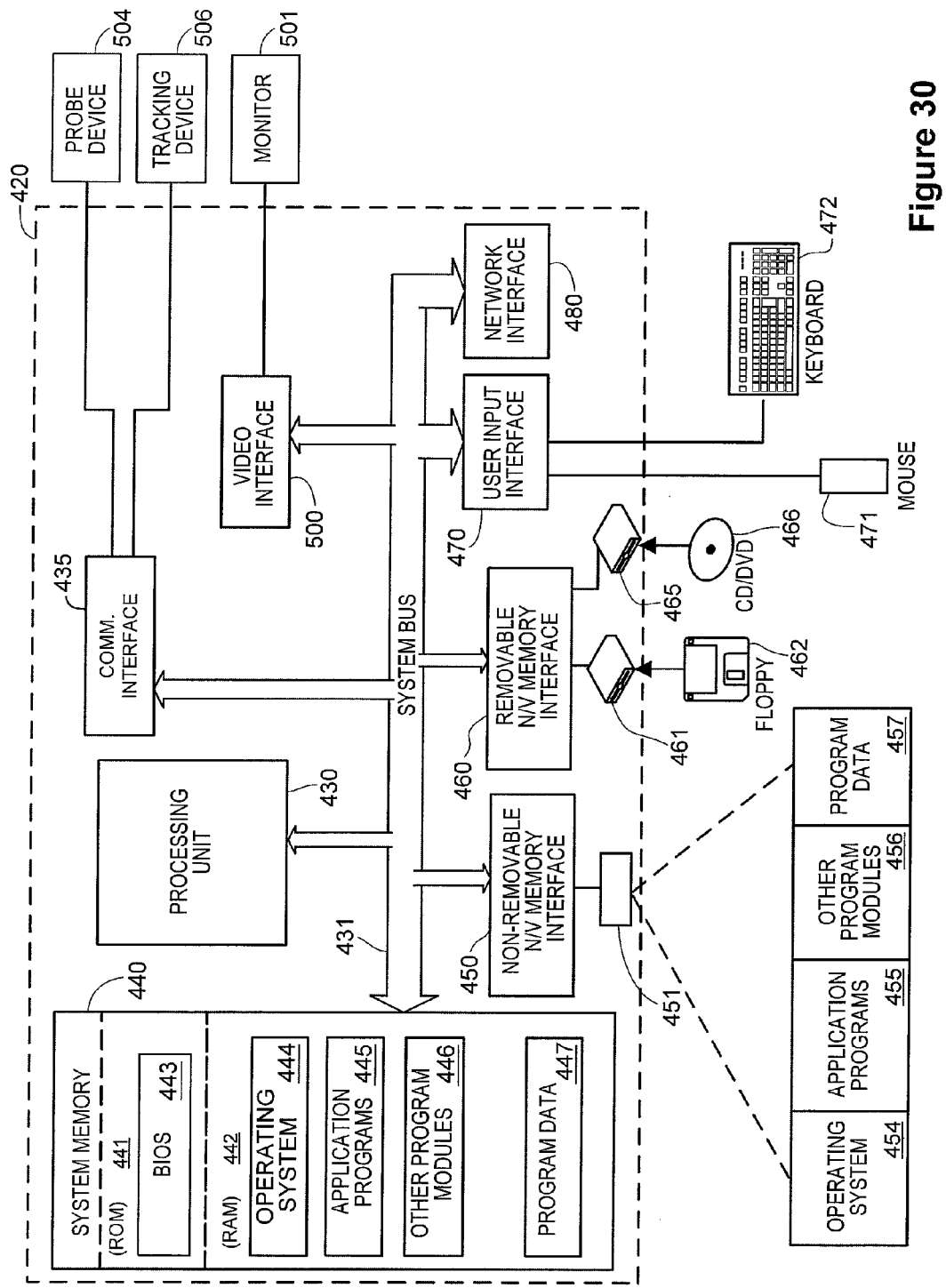
FIG. 30 illustrates an exemplary computer system that may be used to run an embodiment of software in accordance with the presently described system.

FIG. 30 illustrates a logical view of a computing device in the form of a computer 420 that may be used in a hand-held optical probe based imaging system with 3-D tracking facilities. For the sake of illustration, the computer 420 is used to illustrate the principles of the instant disclosure. However, such principles apply equally to other electronic devices having sufficient computing power, including, but not limited to, cellular telephones and personal digital assistants, to name a couple. Components of the computer 420 may include, but are not limited to a processing unit 430, a system memory 440, and a system bus 431 that couples various system components including the system memory 440 to the processing unit 430. The system bus 431 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, front side bus, and Hypertransport™ bus, a variable width bus using a packet data protocol.

Computer 420 may include one or more serial, parallel, or other communication interfaces 435, such as Universal Serial Bus (USB) interfaces, IEEE-1394 (FireWire) interfaces, RS-232 interfaces, RS-423 interfaces, RS-485 interfaces, IEEE-488 (HPIB or GPIB) interfaces, etc. The computer 420 may communicate through the communications interface 435 with, for example, a probe device 504 (e.g., the probe 80 described in detail above) and/or with a tracker device 506 (e.g., the tracking system 200).

Computer 420 typically includes a variety of computer readable media. Computer readable media can be any available media that can be accessed by computer 420 and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 420.

The system memory 440 includes computer storage media in the form of volatile and/or nonvolatile memory such as read only memory (ROM) 441 and random access memory (RAM) 442. A basic input/output system 443 (BIOS), containing the basic routines that help to transfer information between elements within computer 420, such as during start-up, is typically stored in ROM 441. RAM 442 typically contains data and/or program modules that are immediately accessible to and/or presently being operated on by processing unit 430. By way of example, and not limitation, FIG. 30 illustrates operating system 444, application programs 445 (such as one or more modules embodying part or all of the methods of FIGS. 23 and 25-29), other program modules 446 (such as one or more modules embodying part or all of the methods of FIGS. 23 and 25-29), and program data 447.

The computer 420 may also include other removable/non-removable, volatile/nonvolatile computer storage media. By way of example only, FIG. 30 illustrates a hard disk drive 450 that reads from or writes to non-removable, nonvolatile magnetic media, a magnetic disk drive 461 that reads from or writes to a removable, nonvolatile magnetic disk 462, and an optical disk drive 465 that reads from or writes to a removable, nonvolatile optical disk 466 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 451 is typically connected to the system bus 431 through a non-removable memory interface such as interface 450, and magnetic disk drive 461 and optical disk drive 465 are typically connected to the system bus 431 by a removable memory interface, such as interface 460.

The drives and their associated computer storage media discussed above and illustrated in FIG. 30, provide storage of computer readable instructions, data structures, program modules, and other data for the computer 420. In FIG. 30, for example, hard disk drive 451 is illustrated as storing operating system 454, application programs 455, other program modules 456, and program data 457. Note that these components can either be the same as or different from operating system 444, application programs 445, other program modules 446, and program data 447. Operating system 454, application programs 455, other program modules 456, and program data 457 are given different numbers here to illustrate that, at a minimum, they are different copies. A user may enter commands and information into the computer 420 through input devices such as a keyboard 472 and pointing device 471, commonly referred to as a mouse, trackball, or touch pad. Other input devices (not shown) may include a microphone, joystick, game pad, satellite dish, scanner, digital camera, or the like. These and other input devices are often connected to the processing unit 440 through a user input interface 470 that is coupled to the system bus, but may be connected by other interface and bus structures, such as a parallel port, game port or a universal serial bus (USB). A monitor 501 or other type of display device is also connected to the system bus 431 via an interface, such as a video interface 500.

The computer 420 may operate in a networked environment using logical connections to one or more remote computers (not depicted) over a network interface 480, such as broadband Ethernet connection or other known network. The computer 420 may communicate via the network interface 480 with one or more other computers executing one or more software modules embodying a portion of the methods of FIGS. 23 and 25-29, for example to split the processing requirements for real-time data manipulation among multiple computers.

Of course, the methods described herein with reference to FIGS. 23 and 25-29 may include more and/or additional processes and/or data manipulation, may omit processes and/ or data manipulation described herein, and may, in some instances, execute processes and/or data manipulation in an order different than described herein. For example, in some embodiments, one or more software modules for acquiring and/or interpreting data from a probe tracking subsystem may be separate from one or more software modules for acquiring and/or interpreting data received from the detector fibers disposed on the probe. Similarly, some embodiments may have one or more software modules for co-registering location data and detector data. Of course, various functions may be combined into one or more software modules, which may provide advantages with respect to processing speed, memory allocation and/or memory requirements, system responsiveness, algorithm efficiency (i.e., changing the order of the executed instructions), etc. Additionally, while methods described with reference to FIGS. 23 and 25-29 are described as embodied in one or more software applications, a person of ordinary skill in the art will readily appreciate that specialized hardware may be programmed and/or fabricated to replace any aspect otherwise embodied as software.

The invention claimed is:

1. A method of near-infrared optically imaging a three-dimensional object comprising:
generating, using a surface rendering device, a three-dimensional surface mesh corresponding to a surface of a target tissue object;
defining the location of the surface mesh with respect to a reference point;
tracing a hand-held probe on the surface of the target tissue object to collect sensor data on a characteristic of the target tissue object at a plurality of positions on the target object, the hand-held probe having a probe area;
tracking the position and orientation of the hand-held probe with respect to the reference point as the hand-held probe is moved along the surface of the target tissue object;
receiving first tracking data, the first tracking data indicating a first probe location and a first probe orientation;
receiving first sensor data of the target tissue object as detected by the hand-held probe at the first probe location and the first probe orientation;
co-registering the first sensor data and the first tracking data on the surface mesh;
displaying the surface mesh, the surface mesh having the first sensor data projected on the surface mesh over a corresponding first area of the surface mesh, the first area of the surface mesh corresponding to the probe area;
receiving second tracking data, the second tracking data indicating a second probe location and a second probe orientation;
receiving second sensor data of the target tissue object as detected by the hand-held probe at the second probe location and the second probe orientation;
co-registering the second sensor data and the second tracking data on the surface mesh; and
updating the displayed surface mesh to include the first sensor data projected over the first area of the surface mesh and the second sensor data projected on the surface mesh over a corresponding second area of the surface mesh, the second area of the surface mesh corresponding to the probe area.

2. The method of claim 1, wherein the hand-held probe is an optical sub-surface imaging probe that provides sensor data for calculating a value from a set of values including a frequency domain photon migration value, a continuous wave parameter value, or a time domain parameter value.

3. The method of claim 1, wherein tracking the position and orientation of the hand-held probe comprises disposing a first device of a pair of devices on the hand-held probe and a second device of the pair of devices at a fixed location with respect to the hand-held probe, wherein the pair of devices comprises a receiver and a transmitter.

4. The method of claim 1, wherein the three-dimensional surface mesh comprises a plurality of sections and wherein each of the plurality of sections is displayed with default color data prior to acquisition and co-registration of the first sensor data.

5. The method of claim 4, wherein a first subset of the plurality of sections of the surface mesh corresponds to the first area, and wherein each of the plurality of sections not in the first subset is displayed with default data prior to acquisition and co-registration of the second sensor data.

6. The method of claim 1, further comprising generating a probe mesh of the probe surface.

7. The method of claim 1, further comprising acquisition of additional sensor data, co-registration of the additional sensor data, and display of the additional co-registered sensor data.

8. A computer-readable storage medium having stored thereon a plurality of instructions for execution by a processor, the instructions operable to cause the processor to:
generate, using a surface rendering device, a three-dimensional surface mesh corresponding to a surface of a target tissue object;
define the location of the surface mesh with respect to a reference point;
receive near-infrared sensor data collected by a hand-held probe moved along the surface of the target tissue object, the near-infrared sensor data related to a characteristic of the target tissue object, the sensor data for a plurality of positions and corresponding orientations of the hand-held probe on the target tissue object;
receive tracking data about the position and orientation of the hand-held probe with respect to the reference point as the hand-held probe is moved along the surface of the target tissue object;
co-register first sensor data and first tracking data on the surface mesh, the first sensor data a subset of the received near-infrared sensor data, the first tracking data indicating a first probe location and a first probe orientation, the first sensor data of the target tissue object as detected by the hand-held probe at the first probe location and the first probe orientation;
display the surface mesh, the surface mesh having the first sensor data projected on the surface mesh over a corresponding first area of the surface mesh, the first area of the surface mesh corresponding to a probe area;
co-register second sensor data and second tracking data on the surface mesh, the second sensor data a subset of the received near-infrared sensor data, the second tracking data indicating a second probe location and a second probe orientation, the second sensor data of the target tissue object as detected by the hand-held probe at the second probe location and the second probe orientation; and
update the displayed surface mesh to include the first sensor data projected over the first area of the surface mesh and the second sensor data projected on the surface mesh over a corresponding second area of the surface mesh, the second area of the surface mesh corresponding to the probe area.

9. The computer readable storage medium of claim 8, wherein the near-infrared sensor data are received from a hand-held, near-infrared optical sub-surface imaging probe and the near-infrared sensor data are for calculating a value from a set of values including a frequency domain photon migration value, a continuous wave parameter value, or a time domain parameter value.

10. The computer readable storage medium of claim 8, wherein tracking the position and orientation of the hand-held probe comprises disposing a first device of a pair of devices on the hand-held probe and a second device of the pair of devices at a fixed location with respect to the hand-held probe, wherein the pair of devices comprises a receiver and a transmitter.

11. The computer readable storage medium of claim 8, wherein the surface mesh comprises a plurality of sections and wherein each of the plurality of sections is displayed with default color data prior to acquisition and co-registration of the first sensor data.

12. The computer readable storage medium of claim 11, wherein a first subset of the plurality of sections of the surface mesh corresponds to the first area, and wherein each of the plurality of sections not in the subset is displayed with default data prior to acquisition and co-registration of the second sensor data.

13. The computer readable storage medium of claim 8, further comprising instructions that cause the processor to generate a probe mesh of the probe surface.

14. The computer readable storage medium of claim 8, further comprising instructions that cause the processor to acquire additional sensor data, co-register the additional sensor data, and display the additional sensor data.

15. A real-time three-dimensional co-registration near-infrared imaging system, the system comprising:
an imaging device comprising a plurality of detectors disposed on a probe face, of a hand-held probe the probe face having a probe area;
a tracking sub-system operable to track in three dimensions both the position and the orientation of the hand-held probe, the tracking sub-system further operable to report to a computer workstation both the position and the orientation of the hand-held probe; and
a computer processor disposed within the computer workstation and operable to execute a set of instructions stored on a computer-readable storage medium disposed within the computer workstation, the instructions causing the processor to:
generate from information received from a surface rendering device a three-dimensional surface mesh of a target tissue object;
define the location of the three-dimensional surface mesh with respect to a reference point;
receive sensor data collected by the plurality of detectors as the hand-held probe is moved along the surface of the target tissue object, the sensor data related to a characteristic of the target tissue object, the sensor data for a plurality of positions and corresponding orientations of the hand-held probe on the target tissue object;
receive tracking data about the position and orientation of the hand-held probe with respect to the reference point as the hand-held probe is moved along the surface of the target tissue object;
determine from the received tracking data the position and orientation of each of the plurality of detectors with respect to the reference point;
co-register first sensor data and first tracking data on the surface mesh, the first sensor data a subset of the received sensor data, the first tracking data indicating a first probe location and a first probe orientation, the first sensor data of the target tissue object as detected by the hand-held probe at the first probe location and the first probe orientation;
display the surface mesh, the surface mesh having the first sensor data projected on the surface mesh over a corresponding first area of the surface mesh, the first area of the surface mesh corresponding to the probe area;
co-register second sensor data and second tracking data on the surface mesh, the second sensor data a subset of the received sensor data, the second tracking data indicating a second probe location and a second probe orientation, the second sensor data of the target tissue object as detected by the hand-held probe at the second probe location and the second probe orientation; and
update the displayed surface mesh to include the first sensor data projected over the first area of the surface mesh and the second sensor data projected on the surface mesh over a corresponding second area of the surface mesh, the second area of the surface mesh corresponding to the probe area.

16. The computer readable storage medium of claim 15, wherein the sensor data is received from an optical sub-surface imaging probe and the sensor data for are calculating a value from a set of values including a frequency domain photon migration value, a continuous wave parameter value, or a time domain parameter value.

17. The computer readable storage medium of claim 15, wherein tracking the position and orientation of the hand-held probe comprises disposing a first device of a pair of devices on the hand-held probe and a second device of the pair of devices at a fixed location with respect to the hand-held probe, wherein the pair of devices comprises a receiver and a transmitter.

18. The computer readable storage medium of claim 15, wherein the surface mesh comprises a plurality of sections and wherein each of the plurality of sections is displayed with default color data prior to acquisition and co-registration of the first sensor data.

19. The computer readable storage medium of claim 18, wherein a first subset of the plurality of sections of the surface mesh corresponds to the first area, and wherein each of the plurality of sections not in the subset is displayed with default data prior to acquisition and co-registration of the second sensor data.

20. The computer readable storage medium of claim 15, further comprising instructions that cause the processor to generate a probe mesh of a probe surface.

21. The computer readable storage medium of claim 15, further comprising instructions that cause the processor to acquire additional sensor data, co-register the additional sensor data, and display the additional sensor data.

* * * * *